(12) United States Patent
Baldassarre

(10) Patent No.: US 11,931,377 B2
(45) Date of Patent: Mar. 19, 2024

(54) METHODS OF ADMINISTERING INHALED NITRIC OXIDE GAS

(71) Applicant: MALLINCKRODT HOSPITAL PRODUCTS IP LIMITED, Dublin (IE)

(72) Inventor: James S. Baldassarre, Doylestown, PA (US)

(73) Assignee: Mallinckrodt Hospital Products IP Limited (IE)

( * ) Notice: Subject to any disclaimer, the term of this patent is extended or adjusted under 35 U.S.C. 154(b) by 0 days.

(21) Appl. No.: 16/378,361

(22) Filed: Apr. 8, 2019

(65) Prior Publication Data
US 2019/0231814 A1    Aug. 1, 2019

Related U.S. Application Data

(60) Division of application No. 13/683,444, filed on Nov. 21, 2012, now abandoned, which is a division of application No. 12/820,866, filed on Jun. 22, 2010, now abandoned, which is a continuation of application No. 12/494,598, filed on Jun. 30, 2009, now abandoned, said application No. 13/683,444 is a division of application No. 13/651,660, filed on Oct. 15, 2012, now Pat. No. 8,431,163, which is a continuation of application No. 12/821,041, filed on Jun. 22, 2010, now Pat. No. 8,293,284, which is a continuation of application No. 12/494,598, filed on Jun. 30, 2009, now abandoned.

(51) Int. Cl.
| | | |
|---|---|---|
| A61K 33/00 | (2006.01) | |
| A61B 5/00 | (2006.01) | |
| A61B 5/02 | (2006.01) | |
| A61B 5/0205 | (2006.01) | |
| A61B 5/08 | (2006.01) | |
| A61B 8/08 | (2006.01) | |
| A61K 31/04 | (2006.01) | |
| A61K 31/21 | (2006.01) | |
| A61K 45/06 | (2006.01) | |
| A61M 16/00 | (2006.01) | |
| A61M 16/10 | (2006.01) | |
| A61M 16/12 | (2006.01) | |
| A61M 60/139 | (2021.01) | |
| A61M 60/295 | (2021.01) | |
| A61M 60/497 | (2021.01) | |
| A61M 60/841 | (2021.01) | |
| A61M 60/857 | (2021.01) | |
| A61P 9/00 | (2006.01) | |
| A61P 9/10 | (2006.01) | |
| A61P 11/00 | (2006.01) | |
| G06Q 99/00 | (2006.01) | |
| G16H 20/10 | (2018.01) | |

(52) U.S. Cl.
CPC .......... *A61K 33/00* (2013.01); *A61B 5/02007* (2013.01); *A61B 5/0205* (2013.01); *A61B 5/08* (2013.01); *A61B 5/4839* (2013.01); *A61B 5/7275* (2013.01); *A61B 5/7278* (2013.01); *A61B 8/0883* (2013.01); *A61B 8/48* (2013.01); *A61K 31/04* (2013.01); *A61K 31/21* (2013.01); *A61K 45/06* (2013.01); *A61M 16/0057* (2013.01); *A61M 16/104* (2013.01); *A61M 16/12* (2013.01); *A61M 60/139* (2021.01); *A61M 60/295* (2021.01); *A61M 60/497* (2021.01); *A61M 60/841* (2021.01); *A61M 60/857* (2021.01); *G06Q 99/00* (2013.01); *F17C 2201/058* (2013.01); *F17C 2203/0646* (2013.01); *F17C 2221/014* (2013.01); *F17C 2221/03* (2013.01); *F17C 2223/0123* (2013.01); *F17C 2223/036* (2013.01); *F17C 2270/025* (2013.01); *G16H 20/10* (2018.01)

(58) Field of Classification Search
CPC ..... A61B 8/48; A61B 5/02007; A61B 8/0883; A61B 5/08; A61B 5/0205; A61M 2202/0275; C01B 21/24
See application file for complete search history.

(56) References Cited

U.S. PATENT DOCUMENTS

| | | | |
|---|---|---|---|
| 5,485,827 | A | 1/1996 | Zapol et al. |
| 5,558,083 | A | 9/1996 | Bathe et al. |
| 5,651,358 | A | 7/1997 | Briend et al. |
| 5,728,705 | A | 3/1998 | Lawson et al. |
| 5,732,693 | A | 3/1998 | Bathe et al. |
| 5,846,973 | A | 12/1998 | Gehlert et al. |
| 5,873,359 | A | 2/1999 | Zapol et al. |
| 5,890,490 | A | 4/1999 | Aylsworth et al. |
| 6,063,407 | A | 5/2000 | Zapol et al. |
| 6,142,147 | A | 11/2000 | Head et al. |

(Continued)

FOREIGN PATENT DOCUMENTS

| | | |
|---|---|---|
| EP | 0659445 | 6/1995 |
| EP | 0786264 | 7/1997 |

(Continued)

OTHER PUBLICATIONS

Wanstall et al. (Drugs 1998;56(6):989-1007) (Year: 1998).*

(Continued)

*Primary Examiner* — Ernst V Arnold
(74) *Attorney, Agent, or Firm* — Fish & Richardson P.C.

(57) ABSTRACT

The invention relates methods of reducing the risk or preventing the occurrence of an adverse event (AE) or a serious adverse event (SAE) associated with a medical treatment comprising inhalation of nitric oxide.

43 Claims, No Drawings

(56) References Cited

U.S. PATENT DOCUMENTS

| | | | |
|---|---|---|---|
| 6,259,654 | B1 | 7/2001 | De La Huerga |
| 6,601,580 | B1 | 8/2003 | Bloch et al. |
| 7,114,510 | B2 | 10/2006 | Peters et al. |
| 7,557,087 | B2 | 7/2009 | Rothbard et al. |
| 8,282,966 | B2 | 10/2012 | Baldassarre et al. |
| 8,293,284 | B2 | 10/2012 | Baldassarre et al. |
| 8,431,163 | B2 | 4/2013 | Baldassarre et al. |
| 8,795,741 | B2 | 8/2014 | Baldassarre et al. |
| 8,846,112 | B2 | 9/2014 | Baldassarre et al. |
| 2002/0185126 | A1 | 12/2002 | Krebs |
| 2003/0062043 | A1 | 4/2003 | Fine et al. |
| 2003/0131848 | A1 | 7/2003 | Stenzler |
| 2004/0106954 | A1 | 6/2004 | Whitehurst et al. |
| 2008/0193566 | A1 | 8/2008 | Miller et al. |
| 2009/0018136 | A1 | 1/2009 | Oppenheimer et al. |
| 2009/0029371 | A1 | 1/2009 | Elliott |
| 2009/0149541 | A1 | 6/2009 | Stark et al. |
| 2009/0176772 | A1 | 7/2009 | Blackburn et al. |
| 2010/0130500 | A1 | 5/2010 | Kakkis |
| 2010/0256237 | A1 | 10/2010 | Auten et al. |
| 2013/0074839 | A1 | 3/2013 | Baldassarre |

FOREIGN PATENT DOCUMENTS

| | | |
|---|---|---|
| EP | 1516639 | 3/2005 |
| EP | 1682672 | 10/2009 |
| WO | WO 1992/010228 | 6/1992 |
| WO | WO 1995/026768 | 10/1995 |
| WO | WO 2005/004884 | 4/2005 |
| WO | WO 2006/127907 | 11/2006 |
| WO | WO 2010/019540 | 2/2010 |

OTHER PUBLICATIONS

Bernasconi et al. (Images Paediatr Cardiol. 2002;4(1):4-29) (Year: 2002).*

INOmax label 2007; 2 pages (Year: 2007).*

Dash et al. (Br Heart J. 1980;44:322-9) (Year: 1980).*

Shapiro et al. (Advances in PH Journal 2006;5(1): 13 pages). (Year: 2006).*

Pahal et al. Idiopathic Pulmonary Artery Hypertension (IPAH) [online] retrieved on Oct. 15, 2019 from: https://www.ncbi.nlm.nih.gov/books/NBK482251/; Feb. 2019; 7 pages. (Year: 2019).*

Ilsar et al. (Abstract of: Heart Lung Circ Jan. 2010;19(1):38-42; 2 pages) (Year: 2010).*

Greenough, A. (Neonatal Respiratory Disorders 2ed, 2003; p. 187) (Year: 2003).*

Jaypee Brothers (Pediatric and Neonatal Mechanical Ventilation 2006; Jaypee Brothers Publishers pp. 155-156). (Year: 2006).*

Allen et al. (Ann Thorac Surg 1997;64:1381-1388). (Year: 1997).*

"Inhaled Nitric Oxide and Hypoxic Respiratory Failure in Infants With Congenital Diaphragmatic Hernia," The Neonatal Inhaled Nitric Oxide Study Group (NINOS), Pediatrics, vol. 99, No. 6, pp. 838-845 (1997).

"Use of Inhaled Nitric Oxide." American Academy of Pediatrics—Committee on Fetus and Newborn. Pediatrics vol. 106. No. 2. pp. 344-345 (2000).

'ClinicalTrials.gov' [online]. "High-Frequency Oscillatory Ventilation Associated With Inhaled Nitric Oxide in Children," Jun. 2009, [retrieved on Nov. 3, 2015]. Retrieved from the Internet: URL<https://clinicaltrials.gov/ct2/show/NCT00924846>, 3 pages.

"Giving Medication to Children: Q & A with Dianne Murphy, M.D.," FDA Consumer Health Information, U.S. Food and Drug Administration, Jun. 2009, 1-3.

AARC Clinical Practice Guideline, "Neonatal Time-Triggered, Pressure-Limited, Time-Cycled Mechanical Ventilation," Respiratory Care, Aug. 1994, 39(8): 808-816.

AARC, Mechanical Ventilation: Ventilatory Techniques, Pharmacology, and Patient Management Strategies Part II, Respiratory Care, May 1996, 41(5): 134 pages.

AARC, Proceedings from a special symposium on Use of Inhaled Nitric Oxide in the Hypoxic Newborn, Presented at the 51st International Respiratory Congress of the American Association for Respiratory Care in San Antonio, Texas on Dec. 2005, 41 pages.

Abman et al., "Inhaled Nitric Oxide Therapy of Pulmonary Hypertension and Respiratory Failure in Premature and Term Neonates," Advances in Pharmacology, 1995, 34: 457-474.

Adatia et al., "Inhaled nitric oxide and hemodynamic evaluation of patients with pulmonary hypertension before transplantation," J. Am. Coll. Cardiol., 1995, 25: 1656-64.

Adhikari et al., "Effect of nitric oxide on oxygenation and mortality in acute lung injury: systematic review and meta-analysis," BMJ, Mar. 23, 2007, pp. 1-8.

Advances in Pulmonary Hypertension, vol. 7(4), pp. 1-418, Winter 2008-2009 (entire issue).

Aikio, "Pulmonary Nitric Oxide In Preterm And Term Infants With Respiratory Failure," Oulun Yliopisto, Oct. 2002, 74 pages.

Air Liquide Medicinal, VasoKINOX, retrieved from the Internet: URL<http://www.airliquidemedicin.al.es/file/otherelement/pj/vasokinox46604.pdf>, May 2008, 9 pages.

Akmal et al., "Role of nitric oxide in management of acute respiratory distress syndrome," Annals of Thoracic Medicine, Jul.-Sep. 2008, 3(3): 100-103.

Al-Alaiyan et al., "Inhaled nitric oxide in persistent pulmonary hypertension of the newborn refractory to high-frequency ventilation," Crit. Care, vol. 3, No. 1, pp. 7-10 (1999).

Allen et al., "Inhaled Nitric Oxide in Preterm Infants," Evidence Report/Technology Assessment, No. 195. (Prepared by Johns Hopkins University Evidence-based Practice Center under Contract No. 290-2007-10061-1). AHRQ Publication No. 11-E001. Rockville, MD: Agency for Healthcare Research and Quality, Oct. 2010, 315 pages.

Aloya et al., "Recomendaciones para la utilización del óxido nítrico inhalado en patología neonatal," An. Pediatr. Barc, 2006, 64(3): 260-6 (English abstract included).

Ameduri et al., Heart Failure in Children, MED-Continuing Medical Education, University of Minnesota. Jul. 29, 2009, (cited Nov. 12, 2010); available from URL: tlp://www.cme.umn.edu/prod/groups/med/@pub/@med/@cme/documents/content/med_content_124593.pdf.

Amended INOT22 Protocol, Excerpt from prosecution history of U.S. Pat. No. 8,795,741 (submitted as Appendix 3 to Dr. Baldassarre Declaration under 37 C.F.R. § 1.131), pp. 1-60.

Angeja et al., "Evaluation and Management of Diastolic Heart Failure," Circulation, 2003, 107: 659-663.

Arcasoy et al., "Echocardiographic Assessment of Pulmonary Hypertension in Patients with Advanced Lung Disease," Am. J. Respir. Crit. Care Med., 2003, 167: 735-740.

Archer et al., "An evidence-based approach to the management of pulmonary arterial hypertension," Curr. Opin. Cardiol., 2006, 21:385-392.

Argenziano et al., "Inhaled Nitric Oxide is not a Myocardial Depressant in a Porcine Model of Heart Failure," The Journal of Thoracic and Cardiovascular Surgery, vol. 115, pp. 700-704 (1998).

Argenziano et al., "Randomized, Double-Blind Trial of Inhaled Nitric Oxide in LVAD Recipients With Pulmonary Hypertension," Ann. Thorac. Surg., 1998, 65: 340-5.

Arul et al., "Inhaled Nitric Oxide for Preterm Neonates," Clin. Perinatol., 2009, 36: 43-61.

Atz et al., "Combined Effects of Nitric Oxide and Oxygen During Acute Pulmonary Vasodilator Testing," Journal of the American College of Cardiology (JACC), vol. 33, No. 3, pp. 813-819 (1999).

Atz et al., "Inhaled nitric oxide in the neonate with cardiac disease," Seminars in Perinatology, vol. 21(5), pp. 441-455 (1997).

Atz et al., "Diagnostic and Therapeutic Uses of Inhaled Nitric Oxide in Neonatal Ebstein's Anomaly," The American Journal of Cardiology, Apr. 1, 2003, 91: 906-908.

AU 2009202685 Office Action dated Jun. 17, 2010 (3 pages).

AU 2009202685 Office Action Response dated Jul. 29, 2010, 19 pages.

Australia INOmax Label/Product Information, Nov. 2007, 4 pages.

(56) References Cited

OTHER PUBLICATIONS

Autorisation De Mise Sur Le Marche for VasoKINOX 450 ppm mole/mole issued by the Belgian Federal Agency for Drug and Medical Products, dated Jul. 14, 2008, (37 pages, including English translation).
Azeka et al., "Effects of Low Doses of Inhaled Nitric Oxide Combined with Oxygen for the Evaluation of Pulmonary Vascular Reactivity in Patients with Pulmonary Hypertension," Pediatric Cardiol., vol. 23, pp. 20-26 (2002).
Balaguru et al., "Management of Heart Failure in Children," Curr. Probl. Pediatr., Jan. 2000, 30: 5-30.
Baldassarre, "Inhaled Nitric Oxide (INO) in Hypoxic Respiratory Failure, Study description, study sponsored by INO Therapeutics," ClinicalTrials.gov Identifier NCT00922532, 4 pages (2009).
Ballard et al., "Surfactant Function and Composition in Premature Infants Treated With Inhaled Nitric Oxide," Pediatrics, Aug. 2007, 120(2): 346-353.
Balzer et, al., "Inhaled Nitric Oxide as a Preoperative Test (INOP Test I) The INOP Test Study Group," Circulation, Sep. 2002, 106(suppl I): I-76-I-81.
Banjar, "Diagnosis and Management of Pulmonary Arterial Hypertension in the Pediatric Population (PH)," Bahrain Medical Bulletin, Dec. 2008, 30(4): 1-19.
Barrington et al., "Inhaled Nitric Oxide for Preterm Infants: A Systematic Review," Pediatrics, vol. 120; pp. 1088-1099, DOI: 10.1542/peds (2007).
Barrington et al., "Inhaled nitric oxide for respiratory failure in preterm infants (review)," The Cochrane Collaboration, Wiley Publishers, 3 pages (2009).
Barst et al., "Nitric Oxide in Combination with Oxygen versus Either Oxygen Alone or Nitric Oxide Alone for Acute Vasodilator Testing in Children with Pulmonary Hypertension: A Multicenter, Randomized Study," INO Therapeutics/ lkaria, Baltimore Convention Center, May 3, 2009, 2 pages, Abstract, downloaded Jul. 2, 2009 from hllp://127.0.0.1:9080/ PAS09A1/view.y?nu=PAS09L1_1507.
Barst et al., "Vasodilator Testing with Nitric Oxide and/or Oxygen in Pediatric Pulmonary Hypertension." Pediatric Cardiology; Published online Apr. 20, 2010, 598-606, 9 pages.
Baysal, "Nitric Oxide II: Therapeutic Uses and Clinical Applications," Turk. J. Med. Sci., 2002, 32: 1-6.
Bates, "Inhaled Nitric Oxide: A Selective Pulmonary Vasodilator," 2004, 9 pages.
Beasley et al., "Withdrawal of Fenoterol and the End of the New Zealand Asthma Mortality Epidemic," Int. Arch. Allergy Immunol., 1995, 107: 325-327.
Beggs et al., "Cardiac Failure in Children," 17th Expert Committee on the Selection and Use of Essential Medicines, Geneva, Mar. 2009, 31 pages.
Beghetti et al., "Inhaled nitric oxide and congenital cardiac disease," Cardiol. Young, vol. 11, pp. 142-152 (2001).
Beghetti, "Inhaled Nitric Oxide Can Cause Severe Systemic Hypotension," J. Pediatr., 1997, 130: 844.
Behera et al., "Nesiritide Improves Hemodynamics in Children with Dilated Cardiomyopathy: A Pilot Study," Pediatr. Cardiol., vol. 30, pp. 26-34 (2009).
Beloucif et al., "A European survey of the use of inhaled nitric oxide in the ICU," Intensive Care Med, 1998, 24: 864-877.
Berger et al., "Clinical features of paediatric pulmonary hypertension: a registry study," Lancet, Feb. 11, 2012, 379: 537-46.
Bernasconi et al., "Inhaled Nitric Oxide Applications in Paediatric Practice," Images in Paediatric Cardiology, 2002, 4-29.
Bernd Mayer, Editor, Nitric Oxide: Handbook of Experimental Pharmacology, 2000, Chapter 17, 412-414.
Berner et al., "Inhaled Nitric Oxide to Test the Vasodilator Capacity of the Pulmonary Vascular Bed in Children With Long-Standing Pulmonary Hypertension and Congenital Heart Disease," The American Journal of Cardiology, Mar. 1, 1996, 77: 532-535.
Bhagavan et al., "Potential role of ubiquinone (coenzyme O10) in pediatric cardiomyopathy," Clinical Nutrition, vol. 24, pp. 331-338 (2005).
Bichel et al., "Successful weaning from cardiopulmonary bypass after cardiac surgery using inhaled nitric oxide", Pediatric Anesthesia, vol. 7, pp. 335-339 (1997).
Bin-Nun et al., "Role of iNO in the modulation of pulmonary vascular resistance," Journal of Perinatology, vol. 28, pp. S84-S92 (2008).
Blaise et al., "Nitric oxide, cell signaling and cell death," Toxicology 208, 2005, 177-192.
Bland, "Pulmonary vascular dysfunction in preterm lambs with chronic lung disease," Am J Physical Lung Cell Mol. Physiol., vol. 285: L76-L85 ( 2003).
Bloch et al., "Inhaled NO as a therapeutic agent," Cardiovasc. Res. 2007, vol. 75(2), pp. 339-348 (Jul. 15, 2007).
Bocchi et al., "Inhaled Nitric Oxide Leading to Pulmonary Edema in Stable Severe Heart Failure," The American Journal of Cardiology, vol. 74, pp. 70-72 (1994).
Bolooki. Clinical Application of the Intra-Aortic Balloon Pump. 3rd Ed., pp. 252-253 (1998).
Bouhemad et al., "Echocardiographic Doppler Assessment of Pulmonary Capillary Wedge Pressure in Surgical Patients with Postoperative Circulatory Shock and Acute Lung Injury," Anesthesiology, 2003, 98: 1091-100.
Boyle, "Nitric Oxide Delivery Via Nasal Cannula," Retrieved from the Internet: URL<http://www.rtmagazine.com/2007/02/nitric-oxide-delivery-via-nasal-cannula/>, Feb. 7, 2007, 6 pages.
Branson, "Delivery of Inhaled Nitric Oxide," AARC Symposium, 2000, 21-39.
Branson. "Inhaled Nitric Oxide in Adults." The Science Journal of the American Association for Respiratory Care 1997 Open Forum Abstracts. Dec. 7, 1997. 2 pages. retrieved at «http://www.rcjournal.com/abstracts/1997/? id=A00000929» on Dec. 22, 2010.
Braunwald. Heart Failure. Chapter 233 of Harrison's Principles of Internal Medicine. 14th Edition. pp. 1287-1291 and 1360 (1998).
Brief on Appeal filed Oct. 4, 2011 in U.S. Appl. No. 12/820,866, 211 pages.
Bublik et al., "Pediatric cardiomyopathy as a chronic disease: A perspective on comprehensive care programs. Progress in Pediatric." Pediatric Cardiology. vol. 25. pp. 103-111 (2008).
Budts et al., "Residual pulmonary vasoreactivity to inhaled nitric oxide in patients with severe obstructive pulmonary hypertension and Eisenmenger syndrome." Heart. vol. 86. pp. 553-558 (2001).
Burkhoff et al., "Why does pulmonary venous pressure rise after onset of LV dysfunction: a theoretical analysis," Am. J_ Physiol., 34:H1819-H1828 (1993).
Burrows et al., "Pulmonary hypertension in children: perioperative management," Can. Anaesth. Soc. J., 1986, 33(5): 606-28.
Bushman, "Essentials of Nitric Oxide for the Pediatric (Cardiac) Anesthesiologist," Seminars in Cardiothoracic and Vascular Anesthesia, Mar. 2001, 5(1): 79-90.
Butt, "Recent Advances in Paediatric Ventilation," Critical Care & Resuscitation, 1999, 1: 85-92.
Canadian Intellectual Property Office, Requisition by the examiner in CA Appl. 2,671,029; Apr. 25, 2013; 24 pp.
Canadian Office Action dated May 31. 2011 for Canadian Patent Application No. 2671029. a counterpart foreign application of U.S. Appl. No. 12/494,598.
Carcillo et al., "Clinical practice parameters for hemodynamic support of pediatric and neonatal patients in septic shock," Crit. Care Med., 2002, 30(6): 1365-1378.
Cardinal Intellectual Property, Patent Search Report, dated May 12, 2014, 17 pages.
Carlquist, "Neonatal Use of Inhaled Nitric Oxide," Department of Neonatology, Astrid Lindgren Children's Hospital, 2012, 42 pages.
Center for Drug Evaluation and Research, Application No. NDA 20845, INOMAX, Final Printed Labeling, Retrieved from the Internet: URL<http://www.accessdata.fda.gov/drugsatfda_docs/nda/99/20845_inomax_prntlbl.pdf>, Aug. 9, 2000, 8 pages.
Chemla et al., "Haemodynamic evaluation of pulmonary hypertension," Eur. Respir., 2002, 20: 1314-1331.

(56) References Cited

OTHER PUBLICATIONS

Clark et al., "Low-Dose Nitric Oxide Therapy for Persistent Pulmonary Hypertension: 1-Year Follow-up." Journal of Perinatology. vol. 23. pp. 300-303 (2003).
Clark et al., "Low-Dose Nitric Oxide Therapy for Persistent Pulmonary Hypertension of the Newborn," New England J. Med., 2000, 342: 469-474.
Clutton-Brock, Two Cases of Poisoning by Contamination of Nitrous Oxide with Higher Oxides of Nitrogen During Anesthesia; Brit. J Anaesth. 39:388-392 (1967).
Cockrill et al., "Comparison of the Effects of Nitric Oxide, Nitroprusside, and Nifedipine on Hemodynamics and Right Ventricular Contractibility in Patients With Chronic Pulmonary Hypertension." Chest. vol. 119. No. 1. pp. 128-136 (2001).
Communication from Canadian Intellectual Property Office dated Mar. 19, 2013, enclosing Protest from Robic regarding Canadian patent application No. 2,671,029 (42 pages).
Communication from Canadian Intellectual Property Office dated Mar. 19, 2013, enclosing Protest from Torys LLP regarding Canadian patent application No. 2,671,029 (36 pages).
Comparison of Supplemental Oxygen and Nitric Oxide for Inhalation in the Evaluation of the Reactivity of the Pulmonary Vasculature During Acute Pulmonary Vasodilator Testing. http://clinicaltrials.gov/archive/NCT00626028/2009_01_12 Jan. 12, 2009.
Cornfield et al., "Randomized, Controlled Trial of Low-dose Inhaled Nitric Oxide in the Treatment of Term and Near-term Infants with Respiratory Failure and Pulmonary Hypertension," Pediatrics, 1999, 104: 1089-1094.
Corning, "Nitric Oxide," RC Educational Consulting Services, Inc., 2003, 1-14.
Cox et al., "Factors Associated with Establishing a Causal Diagnosis for Children with Cardiomyopathy," Pediatrics, vol. 118, No. 4, pp. 1519-1531 (2006).
Creagh-Brown et al., "Bench-to-bedside review: Inhaled nitric oxide therapy in adults," Critical Care, May 2009, 13: 1-8.
Critical Care Medicine Department, Critical Care Therapy and Respiratory Care Section, "Nitric Oxide Therapy," Policy No. 2, May 2000, 13 pages.
Cujec et al., "Inhaled Nitric Oxide Reduction in Systolic Pulmonary Artery Pressure is Less in Patients with Decreased Left Ventricular Ejection Fraction," Canadian Journal of Cardiology, vol. 13(9), pp. 816-824 (1997).
Curriculum vitae of Dr. Edward Lawson, dated Feb. 4, 2016, 27 pages.
Curriculum Vitae of Dr. Maurice Beghetti, 1-47.
Curriculum Vitae of Geoffrey L. Rosenthal, M.D., Ph.D., Aug. 14, 2015, 1-19.
Cuthbertson et al., "UK guidelines for the use of inhaled nitric oxide therapy in adults ICUs," Intensive Care Med., vol. 23, Springer-Verlag, pp. 1212-1218 (1997).
Daftari et al., "Initial Experience with Sildenafil, Bosentan, and Nitric Oxide for Pediatric Cardiomyopathy Patients with Elevated Pulmonary Vascular Resistance before and after Orthotropic Heart Transplantation," Journal of Transplantation, Jan. 2010, 2010: 1-6.
Davidson et al., "Inhaled nitric oxide for the early treatment of persistent pulmonary hypertension of the term newborn: a randomized, double-masked, placebo-controlled, dose-response, multi-center study," Pediatrics, vol. 101 (3 Pt 1), pp. 325-334 (1998).
Davidson et al., "Safety of Withdrawing Inhaled Nitric Oxide Therapy in Persistent Pulmonary Hypertension of the Newborn," Pediatrics, vol. 104, No. 2, pp. 231-236 (1999).
Davidson et al., "Inhaled Nitric Oxide for the Early Treatment of Persistent Pulmonary Hypertension of the Term Newborn: A Randomized, Double-Masked, Placebo-Controlled, Dose-Response, Multicenter Study," Pediatrics, 1998, 101: 325-334.
Day et al., "Pulmonary Vasodilatory Effects of 12 and 60 Parts Per Million Inhaled Nitric Oxide in Children with Ventricular Septal Defect," The American Journal of Cardiology, vol. 75, pp. 196-198 (1995).
Day, "Right ventricular size is acutely decreased by inhaled nitric oxide in newborns with pulmonary hypertension," American Journal of Perinatology, 1998, 15(7): 445-451 (Abstract Only).
De Oliveira et al., "Inhaled Nitric Oxide In The Management Of Persistent Pulmonary Hypertension Of The Newborn: A Meta-Analysis," Rev. Hosp. Clin. Fac. Med. S. Paulo, Jul.-Aug. 2000, 55 (4):145-154.
Declaration of Dr. Edward Lawson, dated Mar. 22, 2016, pp. 1-29.
Declaration of Dr. Maurice Beghetti in Support of Petition for Inter Partes Review of U.S. Pat. No. 8,282,966, dated Dec. 31, 2015, pp. 1-55.
Declaration of Dr. Maurice Beghetti in Support of Petition for Inter Partes Review of U.S. Pat. No. 8,431,163, dated Dec. 31, 2014, pp. 1-53.
Declaration of Dr. Maurice Beghetti in Support of Petition for Inter Partes Review of U.S. Pat. No. 8,846,112, dated Dec. 31, 2014, pp. 1-54.
Declaration of Geoffrey L. Rosenthal, M.D., Ph.D. in Support of Patent Owner's Preliminary Response to Praxair's Petition for Inter Partes Review of U.S. Pat. No. 8,282,966, dated Jun. 30, 2016, pp. 1-41.
Declaration of James S. Baldassarre, M.D., Under 37 C.F.R. § 1.132, dated Dec. 4, 2013, submitted during prosecution of U.S. Pat. No. 8,846,112, 8 pages.
Definition of "Contraindication" on Medicine.net.com, Retrieved from the Internet: URL<https://web.archive.org/web/20060812144659/http://www.medterms.com/script/main/art.asp?articlekey=17824>, Aug. 12, 2006, 2 pages.
Definition of Contraindication, MedlinePlus, Retrieved from the Internet: URL<https://web.archive.org/web/20090324033016/http://www.nlm.nih.gov/medlineplus/ency/article/002314.htm>, Mar. 24, 2009, 2 pages.
Delivery of Inhaled Nitric Oxide Therapy through an Adult or Pediatric Nasal Cannula, Reference: UTMB Respiratory Care Services Reviewed: May 31, 2005.
Desai et al., "Ventilatory Strategies and Adjunctive Therapy in ARDS," Indian J. Pediatr,, Aug. 2006, 73(8): 661-668.
Description of the clinical trial NCT00626028 published online on the website http://clinicaltrials.gov/archive/ NCT00626028; Feb. 28, 2008.
Dickstein et al., "A Theoretic Analysis of the Effect of Pulmonary Vasodilation on Pulmonary Venous Pressure: Implications for Inhaled Nitric Oxide Therapy," The Journal of Heart and Lung Transplant, pp. 715-721 (1996).
Dorland, "The American Illustrated Medical Dictionary," 7th edition, W.B. Saunders Company, p. 113 (1914).
Dorling, "Neurodevelopmental outcome following Nitric Oxide Therapy for Persistent Pulmonary Hypertension in Term Newborn Infants," Neonatal Intensive Care Unit, Leicester Royal Infirmary, Aug. 8, 2003, modified Nov. 12, 2003, 3 pages.
Douwes et al., "The Maze of Vasodilator Response Criteria," Published online: Nov. 26, 2010, Pediatr. Cardiol., vol. 32, pp. 245-246 (2011).
Drinkwater et al., "Modified Norwood operation for hypoplastic left heart syndrome," Ann. Thorac. Surg., 2001, 72: 2081-2087.
Durmowicz, "Pulmonary Edema in 6 Children With Down Syndrome During Travel to Moderate Altitudes," Pediatrics, Aug. 2001, 108: 443-447.
Ehrenkranz, "Inhaled Nitric Oxide in Full-Term and Nearly Full-Term Infants with Hypoxic Respiratory Failure," The Neonatal Inhaled Nitric Oxide Study Group, N. Engl. J_ Med., vol. 336, No. 9, pp. 597-605 (1997).
Elbl et al., "Long-term serial echocardiographic examination of late anthracycline cardiotoxicity and its prevention by dexrazoxane in paediatric patients," Eur. J_ Pediatr., vol. 164, pp. 678-684 (2005).
El-Khuffash, "Are B-type natriuretic peptide (BNP) and N-terminal-pro-BNP useful in neonates?" Arch. Dis. Child Fetal Neonatal Ed., 2007, 92: F320-F324.
El-Segaier et al., "Nitric oxide in neonatal transposition of the great arteries," Acta Paediatrica, 2005, 94: 912-916.
Elshamaa et al., "Plasma Nitric Oxide Level in Myocardial Disorders with Left Ventricular Diastolic Dysfunction," J. Med. Sci., May-Jun. 2006, 6(3): 439-444.

(56) References Cited

OTHER PUBLICATIONS

EP 09251949 Office Action dated Oct. 11, 2010, 5 pages.
Eunice Kennedy Shriver National Institute of Child Health and Human Development (NICHD), NCT00005773 at ClinicalTrials.gov (2008).
European Patent Office minutes of oral proceedings in EP 09 251 949.5, with allowable claims (7 pages), dated May 23, 2012.
Farrow et al., "The Diseases Treated with ECMO: Focus on PPHN," Semin. Perinatal., 2005, 29: 8-14.
Fauci et al., Harrison's Principles of Internal Medicine, pp. 1287-1291 and 1360, 12th edition, McGraw Hill (1998).
FDA, "What is a Serious Adverse Event?" Retrieved from the Internet: URL <http://web.archive.org/web/2009061102209/http://www.fda.gov.Safety/MedWatch/HowToReport/ucm053087.htm>, Jun. 11, 2009, 2 pages.
Federal Agency for Medicines and Health Products (European Union), Public Assessment Report, Decentralized Procedure, VasoKINOX 450 ppm mole/mole, inhalation gas, cylinder, Nitric Oxide; Jul. 14, 2008; 34 pages.
Federal Regulations 21 CFR Part 312, «http://www.gcrc.uci.edu/rsa/aer.cfm».
Ferguson et al., "Inhaled nitric oxide for hypoxemic respiratory failure: Passing bad gas?," Canadian Medical Association Journal, vol. 162 (1), pp. 85-86 (2000).
Fernandez-Perez et al., "Inhaled Nitric Oxide for Acute Right-Ventricular Dysfunction After Extrapleural Pneumonectomy," Respir. Care, 2006, 51(10): 1172-1176.
Field, "Neonatal Ventilation With Inhaled Nitric Oxide Versus Ventilatory Support Without Inhaled Nitric Oxide for Preterm Infants With Severe Respiratory Failure: The INNOVO Multicentre Radomised Controlled Trial (ISRCTN 17821339)," Pediatrics Journal, vol. 115, pp. 926-936 (2005) DOI: 10.1542/peds.2004-1209.
Figure from Dr. Green's presentation given Jan. 10, 2011; 1 page.
Findlay, "Paradoxical Haemodynamic Response to Inhaled Nitric Oxide," International Journal of Intensive Care GB, vol. 5, No. 4, pp. 134-139 (1998).
Finer et al., "Randomized, Prospective Study of Low-Dose Versus High-Dose Inhaled Nitric Oxide in the Neonate With Hypoxic Respiratory Failure," Pediatrics, vol. 108, No. 4, pp. 949-955 (2001).
Finer et al., "Nitric oxide for respiratory failure in infants born at or near term," The Cochrane Library, 2006, 4: 46 pages.
Fioretto et al., "Acute and sustained effects of early administration of inhaled nitric oxide to children with acute respiratory distress syndrome," Pediatr. Crit. Care Med., 2004, 5(5): 469-474.
Fish & Richardson P.C., Express Abandonment in U.S. Appl. No. 12/820,866, filed Dec. 3, 2012 (1 page).
Fish & Richardson P.C., Statement of the Substance of the Interview and Comments on Examiner's Interview Summary, in U.S. Appl. No. 12/821,020, dated Jan. 25, 2012, filed Feb. 27, 2012 (7 pages).
Fish & Richardson P.C., Supplemental Remarks in U.S. Appl. No. 12/821,020, filed May 9, 2012 (22 pages).
Fish & Richardson, Brief on Appeal in U.S. Appl. No. 12/820,866, filed Oct. 4, 2011 (211 pages).
Fish & Richardson, P.C., Amendment in Reply to Office Action in U.S. Appl. No. 12/821,041, dated Jun. 27, 2011, filed Jan. 6, 2012 (155 pages).
Fish & Richardson, P.C., Amendment in Reply to Office Action, in U.S. Appl. No. 12/821,020, dated Jun. 27, 2011, filed Dec. 27, 2011 (31 pages).
Fish & Richardson, P.C., Amendment in Reply to Office Action, in U.S. Appl. No. 12/821,041, dated Jun. 19, 2012, filed Aug. 15, 2012 (17 pages).
Fish & Richardson, P.C., Amendment in Reply, in U.S. Appl. No. 12/821,020, dated Jun. 15, 2012, filed Aug. 15, 2012 (15 pages).
Fish & Richardson, P.C., in U.S. Appl. No. 12/821,041, Supplemental Amendment and Remarks, filed May 11, 2012 (32 pages).
Fish & Richardson, P.C., Reply Brief in U.S. Appl. No. 12/820,866, filed Dec. 16, 2011 (21 pages).
Fish & Richardson, P.C., Statement of Substance of Interview and Comments on Examiner's Interview Summary, in U.S. Appl. No. 12/821,020, filed Apr. 23, 2012 (8 pages).
Fish & Richardson, P.C., Supplement to Reply Brief in U.S. Appl. No. 12/820,866, filed Jan. 3, 2012 (3 pages).
Fish & Richardson, P.C., Supplemental Amendment, in U.S. Appl. No. 12/821,020, filed Apr. 30, 2012 (10 pages).
Fojón et al., "Inhaled Nitric Oxide Through a Noninvasive Ventilation Device to Assess Reversibility of Pulmonary Hypertension in Selecting Recipients For Heart Transplant," Transplantation Proceedings, 2005, 37: 4028-4030.
Fraisse et al., "Acute pulmonary hypertension in infants and children: cGMP-related drugs," Pediatric Cril. Care Med., vol. 11, No. 2 (Suppl.), 4 pages (2010).
Fraisse et al., "Doppler echocardiographic predictors of outcome in newborns with persistent pulmonary hypertension," Cardiol Young. vol. 14(3), pp. 277-283 (2004).
Free Merriam-Webster Dictionary, definition of "supplying", pp. 1-4, downloaded Apr. 22, 2013.
Friesen et al., "Review article: Anesthetic management of children with pulmonary arterial hypertension," Pediatric Anesthesia, 2008 18: 208-216.
Fromm et al., "Congestive Heart Failure and Pulmonary Edema for the Emergency Physician," The Journal of Emergency Medicine, 13(1):71-87 (1995).
Frostell et al., "Inhaled Nitric Oxide: A Selective Pulmonary Vasodilator Reversing Hypoxic Pulmonary Vasoconstriction," Circulation, 1991, 83: 2038-2047.
Germann et al., "Inhaled Nitric Oxide Therapy in Adults: European Expert Recommendations," Intensive Care Med, 2005, 31: 1029-1041.
Ghofrani et al., "Pulmonary Vascular Diseases: Uncertainties in the Diagnosis and Treatment of Pulmonary Arterial Hypertension," Circulation, 2008, 118: 1195-1201.
Giaid et al., "Reduced Expression of Endothelial Nitric Oxide Synthase in the Lungs of Patients With Pulmonary Hypertension," N. Engl. J. Med., Jul. 27, 1995, 333: 214-21.
Gibbs, "Recommendations on the management of pulmonary hypertension in clinical practice," Heart, 2001, 86(Suppl I): il-il3.
Gidding, "The Importance of Randomized Controlled Trials in Pediatric Cardiology," JAMA, 2007, 298: 1214-1216.
Goldstein et al., "Inhaled Nitric Oxide is not a Negative Inotropic Agent in a Porcine Model of Pulmonary Hypertension," Thorac. Cardiovasc. Surg., 1997, 114: 461-6.
Gonzalez et al., "Randomized Controlled Trial of Early Compared with Delayed Use of Inhaled Nitric Oxide in Newborns with a Moderate Respiratory Failure and Pulmonary Hypertension," Journal of Perinatology, 2009, 333(4): 1-5.
Google Book Search: "neonatal respiratory" "nitric oxide" ("Google Book Search 2"), Search Performed on Jun. 1, 2016, 2 pages.
Google Book Search: "neonatal ventilation" "nitric oxide" ("Google Book Search 3"), Search Performed on Jun. 1, 2016, 2 pages.
Google Book Search: "neonatal" "nitric oxide" ("Google Book Search 1"), Search Performed on Jun. 1, 2016, 2 pages.
Gothberg et al., "Residual pulmonary hypertension in children after treatment with inhaled nitric oxide: a follow-up study regarding cardiopulmonary and neurological symptoms," Acta. Paediatr., 2000, 89: 1414-9.
Goyal et al., "Efficacy of nitroglycerin inhalation in reducing pulmonary arterial hypertension in children with congenital heart disease," British Journal of Anesthesia, May 2006, 97(2): 208-14.
Green, "Patent Ductus Arteriosus Demonstrating Shunting of Blood," Figure from presentation given Jan. 10, 2011.
Greenough, "Inhaled nitric oxide in the neonatal period", Expert Opinion on investigational Drugs, Ashley Publications Lid., pp. 1601-1609 pages (2000).
Greenough, Neonatal Respiratory Disorders, 2d ed., 2003, 568 pages.
Griffiths et al. "Inhaled Nitric Oxide Therapy in Adults." New England Journal of Medicine, 2005, 353: 2683-2695.
Guidelines for Industry: Clinical Safety Data Management, «www.fda.gov/downloads/Drugs/GuidanceComplianceRegulatoryInformation/Guidance/ucm073087.pdf», Mar. 1995, 17 pages.

(56) References Cited

OTHER PUBLICATIONS

Gurgueira, "Inhaled nitric oxide: clinical application considerations," J. Pneumologia, Sep.-Oct. 2003, 29(5): 7 pages.
Guyatt et al., "Users' Guide to the Medical Literature: A Manual for Evidenced-Based Clinical Practice," 2d ed., 2008, Chapter 2, pp. 9-16.
Haddad et al., "Use of inhaled nitric oxide preoperatively and in intensive care patients," Anesthesiology, vol. 92, pp. 1821-1825 (2000).
Hare et al., Influence of Inhaled Nitric Oxide on Systemic Flow and Ventricular Filling Pressure in Patients Receiving Mechanical Circulatory Assistance, Circulation, vol. 95, pp. 2250-2253 (1997).
Harvard University Countway Library of Medicine, [HMS] EBM—Evidence-based Medicine, retrieved from the Internet: URL< http://guides.library.harvard.edu/hms/ebm>, Nov. 15, 2015, 1-3.
Hayward et al., "Effect of Inhaled Nitric Oxide on Normal Human Left Ventricular Function," JACC, vol. 30, No. 1, pp. 49-56 (1997).
Hayward et al., "Inhaled nitric oxide in cardiology practice," Cardiovascular Research, vol. 43, pp. 628-638 (1999).
Hayward et al., "Left Ventricular Chamber Function During Inhaled Nitric Oxide in Patients with Dilated Cardiomyopathy," J_ Cardiovascular Pharmacology, vol. 34, Iss. 5, pp. 749-754, Abstract (1999).
Hayward et al., "Inhaled Nitric Oxide in Cardiac Failure: Vascular Versus Ventricular Effects," J. Cardiovascular Pharmacology, 1996, 27: 80-85.
Hayward et al., "Review: Inhaled nitric oxide in cardiology practice," Cardiovascular Research, 1999, 43: 628-638.
Headrick. "Hemodynamic monitoring of the critically ill neonate." J_ Perinat. Neonatal Nurs., vol. 5(4), pp. 58-67 (1992).
Heinonen, "Synchronized Delivery of Inspired Nitric Oxide," Comprehensive Summaries of Uppsala Dissertations from the Faculty of Medicine, 2002, 1162: 1-58.
Henrichsen et al., "Inhaled nitric oxide can cause severe systemic hypotension," J. Pediatrics, 1996, 129(1): 183.
Hess, "Heliox and Inhaled Nitric Oxide," Mechanical Ventilation, Chapter 28 (2001), pp. 454-480.
Hess, "Adverse Effects and Toxicity of Inhaled Nitric Oxide," Respir. Care, 1999, 44(3): 315-329.
Hess, "Use of Inhaled Nitric Oxide in Patients with Acute Respiratory Distress Syndrome," Respiratory Care, May 1996, 41(5): 424-46.
Himashree et al., "Nitric oxide and the respiratory system," Current Science, vol. 85, No. 5, Sep. 10, 2003, pp. 607-614.
Hoehn, "Therapy of pulmonary hypertension in neonates and infants," Pharmacology & Therapeutics, 2007, 114: 318-326.
Hoeper et al., "A Comparison of the Acute Hemodynamic Effects of Inhaled Nitric Oxide and Aerosolized Iloprost in Primary Pulmonary Hypertension," Journal of the American College of Cardiology, Jan. 2000, 35(1): 176-182.
Hoeper et al., "Definitions and Diagnosis of Pulmonary Hypertension," J. of the American College of Cardiology, 2013, 62(25): D42-D50.
Hsu et al., "Heart Failure in Children Part I: History, Etiology, and Pathophysiology," Circ. Heart Fail., 2009, 2: 63-70.
http://www.cc.nih.gov/ccmd/clinical_services.html, page last updated May 19, 2011.
http://www.medterms.com/script/main/art.asp?articlekey=17824, Definition of Contraindication, last Editorial Review Mar. 19, 2012.
Huang et al., "Left Ventricular Dysfunction in Children with Fulminant Enterovirus 71 Infection," Brief Report, Apr. 2002, 34: 1020-4.
Huddleston, "Indications for heart transplantation in children," Progress in Pediatric Cardiology, vol. 26, pp. 3-9 (2009).
Hunt et al., "ACC/AHA 2005 Guideline Update for the Diagnosis and Management of Chronic Heart Failure in the Adult," ACC/AHA Practice Guidelines, American College of Cardiology Foundation and the American Heart Association, 2005, e1-e82.
Hurford et al., "Nitric Oxide," Biology and Pathobiology, Academic Press, Chapter 56, pp. 931-945 (2000).
Husten, "Dronedarone is Less Effective, But Safer Than Amiodarone in Atrial Fibrillation," p. 3, (2009) http://www.npci.org.uk/blog/?p=778.
Ichinose et al., "Inhaled Nitric Oxide: A Selective Pulmonary Vasodilator: Current Uses and Therapeutic Potential," Circulation, 2004, 109: 3106-3111.
Ignarro, "Nitric Oxide Biology and Pathobiology," Academic Press, 2000, 1-13.
Inglessis et al., "Does inhaled nitric oxide support the hemodynamic of spontaneous breathing patients with cardiogenic shock related to right ventricular myocardial infarction? Reply," JACC, vol. 45, No. 6, pp. 965-966 (2005).
Inglessis et al., "Hemodynamic effects of inhaled nitric oxide in right ventricular myocardial infarction and cardiogenic shock," JACC, vol. 44, No. 4, pp. 793-798 (2004).
Inhaled Nitric Oxide by Oxygen Hood in Neonates, from ClinicalTrials.gov, NCT00732537, Aug. 8, 2008.
Inhaled Nitric Oxide in Neonates with Elevated A-a DO2 Gradients Not Requiring Mechanical Ventilation, from ClinicalTrials.gov archive, NCT00041548, Jun. 23, 2005, 2 pages.
*INO Therapeutics LLC and Ikaria, Inc. v. Praxair Distribution, Inc. and Praxair, Inc.*, "Defendant's Initial Invalidity Contentions," C.A. No. 15-170-GMS, dated Dec. 15, 2015, 33 pages.
*INO Therapeutics LLC and Ikaria, Inc. v. Praxair Distribution, Inc. and Praxair, Inc.*, "Defendant's Initial Invalidity Contentions," C.A. No. 15-170-GMS, dated Dec. 15, 2015, Appendix A, 76 pages.
*INO Therapeutics LLC and Ikaria, Inc. v. Praxair Distribution, Inc. and Praxair, Inc.*, "Defendant's Initial Invalidity Contentions," C.A. No. 15-170-GMS, dated Dec. 15, 2015, Appendix B, 1624 pages.
INO Therapeutics, "Comparison of Inhaled Nitric Oxide and Oxygen in Patient Reactivity during Acute Pulmonary Vasodilator Testing," downloaded from clinicaltrials.gov on Apr. 23, 2012; last updated on Oct. 18, 2010.
INO Therapeutics, LLC, "INOflo for Inhalation 800ppm," package leaflet, 2010.
INO Therapeutics, NCT00041548 at ClinicalTrials.gov (2005).
INO Therapeutics, NCT00551642 at ClinicalTrials.gov (2007).
INOmax (nitric oxide) for inhalation 100 and 800 ppm (parts per million), drug label insert, 2007, 2 pages.
INOmax Annex I—Summary Of Product Characteristics; Annex II—Manufacturer(s) Responsible for Batch Release, Conditions or Restrictions Regarding Supply and Use, Other Conditions and Requirements of the Marketing Authorisation, Conditions or Restrictions with Regard to the Safe and Effective Use of the Medicinal Product; Annex III—Labeling and Package Leaflet, Nov. 23, 2009, 1-53.
INOmax® Label, Full Prescribing Information, Oct. 2015, 11 pages.
INOvent delivery system Operation and Maintenance Manual; [online] retrieved on Nov. 20, 2017 from: http://rtasap.com/ppt/inovent.pdf; Feb. 8, 2000; 12 pages. (Year: 2000).
Ivy et al., "Dipyridamole attenuates rebound pulmonary hypertension after inhaled nitric oxide withdrawal in postoperative congenital heart disease," J_Thorac. Cardiovasc. Surg.; vol. 115, pp. 875-882 (1998).
Ivy et al., "Pediatric Pulmonary Hypertension," Journal of the American College of Cardiology, 2013, 62(25): Suppl D, 117-126.
James et al., "Treatment of heart failure in children," Current Pediatrics, vol. 15, 539-548 (2005).
Jonsen et al., "Clinical Ethics: A Practical Approach to Ethical Decisions in Clinical Medicine," 4th ed., McGraw-Hill Health Professions Division, 1998, 14 pages.
JP 2009157623 Office Action dated Feb. 15, 2011, 3 pages.
JP 2009157623 Office Action dated Feb. 23, 2010, 3 pages.
Juliana et al., "Severe Persistent Pulmonary Hypertension of the Newborn in a Setting Where Limited Resources Exclude the use of Inhaled Nitric Oxide: Successful Treatment with Sildenafil," Eur. J. Pediatr., 2005, 164: 626-629.
Kaldjian et al., "A Clinician's Approach to Clinical Ethical Reasoning," JGIM, 2005, 20: 306-311.
Kannan et al., "Nitric Oxide: Biological Role and Clinical Uses," Indian J. Pediatr., 1998, 65: 333-345.

(56) References Cited

OTHER PUBLICATIONS

Katerndahl, "When Plagiarism Becomes Research," Family Practice, 1991, 8(4): 382-383.
Kaulitz et al., "Archives of Disease in Childhood: Current treatment and prognosis in children with functionally univentricular hearts," Arch. Dis. Child., 2005, 90: 757-762.
Kay et al., "Congestive heart failure in pediatric patients," From the Department of Pediatrics, Duke University Medical Center, 2001, by Mosby, Inc., 6 pages.
Kazerooni et al. Cardiopulmonary Imaging 2004, Lippincott Williams & Wilkins, pp. 234-235.
Kazerooni, Cardiopulmonary Imaging 2004, Lippincott Williams & Wilkins, "Left Ventricular Function", pp. 234 and 236 (in part).
Keane et al., NADAS' Pediatric Cardiology, 2nd Edition, 2006, Chapter 10, 10 pages.
Khilnani, "Inhaled Nitric Oxide (INO)," Practical Approach to Pediatric Intensive Care, 2005, 9 pages.
Khilnani, Pediatric & Neonatal Mechanical Ventilation, 1st Ed., 2006, 197 pages.
Kieler-Jensen et al., "Inhaled Nitric Oxide in the Evaluation of Heart Transplant Candidates with Elevated Pulmonary Vascular Resistance," Heart & Lung Transplant, 1994, 13: 366-375.
Kinsella et al., "Early Inhaled Nitric Oxide Therapy in Premature Newborns with Respiratory Failure," N. Engl. J. Med., 2006, 355: 354-64.
Kinsella et al., "Effects of Inhaled Nitric Oxide on Pulmonary Edema and Lung Neutrophil Accumulation in Severe Experimental Hyaline Membrane Disease," Pediatric Research, 1997, 41: 457-463.
Kinsella et al., "Inhaled nitric oxide in premature neonates with severe hypoxaemic respiratory failure: a randomised controlled trial," The Lancet, 1999, 354: 1061-1065.
Kinsella et al., "Inhaled nitric oxide therapy in children," Paediatric Respiratory Reviews, 2005, 6: 190-198.
Klabunde, "Pulmonary Capillary Wedge Pressure," Cardiovascular Physiology Concepts, Retrieved from the Internet: <http://www.cvphysiology.com/Heart%20Failure/HF008.htm>, Apr. 11, 2007, 2 pages.
Konduri et al., "A Randomized Trial of Early Versus Standard Inhaled Nitric Oxide Therapy in Term and Near-Term Newborn Infants with Hypoxic Respiratory Failure," Pediatrics, vol. 113 No. 3, pp. 559-564 (2004).
Konduri, "Early inhaled nitric oxide therapy for term and near-term newborn infants with hypoxic respiratory failure: neurodevelopmental follow-up," J. Pediatr., 2007, 150(3): 235-240, 240.e.1.
Krasuski et al., "Inhaled Nitric Oxide Selectively Dilates Pulmonary Vasculature in Adult Patients With Pulmonary Hypertension, Irrespective of Etiology," Journal of the American College of Cardiology (JACC), vol. 36, No. 7, pp. 2204-2211 (2000).
Krohn, "Effect of inhaled nitric oxide on left ventricular and pulmonary vascular function," The Journal of Thoracic and Cardiovascular Surgery, vol. 117(1), pp. 195-196 (1999).
Kulik, "Inhaled nitric oxide in the management of congenital heart disease," Current Opinion in Cardiology, vol. 11, pp. 75-80 (1996).
Laitinen et al., "Postoperative Nitric Oxide Therapy in Children with Congenital Heart Disease," Scand. Cardiovasc. J., 2000, 34: 149-153.
Lavigne et al., "Cardiovascular Outcomes of Pediatric Seroreverters Perinatally Exposed to HAART," Cardiovascular Toxicology, vol. 4, pp. 187-197 (2004).
Lee & Hayes Amendment in Reply to Office Action in U.S. Appl. No. 12/820,866, dated Jun. 8, 2011, filed Jul. 8, 2011 (23 pages).
Lee & Hayes, Amendment in Reply to Office Action in U.S. Appl. No. 12/820,980, dated Jun. 10, 2011, filed Jul. 11, 2011 (115 pages).
Lee & Hayes, Reply After Final (Accelerated Exam-Transmittal Amendment/Reply) in U.S. Appl. No. 12/820,866 dated Nov. 2, 2010, filed May 2, 2011 (9 pages).
Lee & Hayes, Reply After Final (Accelerated Exam-Transmittal Amendment/Reply) in U.S. Appl. No. 12/820,866 dated Sep. 23, 2010, filed Mar. 1, 2011 (5 pages).
Lee & Hayes, Reply After Final (Accelerated Exam-Transmittal Amendment/Reply) in U.S. Appl. No. 12/820,866 dated Sep. 23, 2010, filed Mar. 1, 2011 (9 pages).
Lee & Hayes, Reply after Final (Accelerated Exam-Transmittal Reply) in U.S. Appl. No. 12/820,980, dated Nov. 2, 2010, filed May 2, 2011 (23 pages).
Lee & Hayes, Reply after Final (Accelerated Exam-Transmittal Reply) in U.S. Appl. No. 12/820,980, dated Nov. 2, 2010, filed Nov. 12, 2010 (53 pages).
Lee & Hayes, Reply Amendment (Accelerated Exam-Transmittal Amendment/Reply) in U.S. Appl. No. 12/820,866 dated Nov. 2, 2010, filed Jan. 14, 2011 (12 pages).
Lee & Hayes, Reply Amendment (Accelerated Exam-Transmittal Amendment/Reply) in U.S. Appl. No. 12/820,866 dated Sep. 23, 2010, filed Oct. 1, 2010 (22 pages).
Lee & Hayes, Reply Amendment in U.S. Appl. No. 12/820,980, dated Aug. 17, 2010, filed Sep. 17, 2010 (25 pages).
Lee & Hayes, Reply Amendment in U.S. Appl. No. 12/821,041, dated Aug. 17, 2010, filed Feb. 14, 2011 (28 pages).
Lee & Hayes, Response to Office Action in U.S. Appl. No. 12/821,020, dated Aug. 13, 2010, filed Feb. 14, 2011 (18 pages).
Lee & Hayes, Supplemental Reply Amendment in U.S. Appl. No. 12/821,020, filed Apr. 12, 2011 (9 pages).
Lee & Hayes, Supplemental Reply Amendment in U.S. Appl. No. 12/821,041, dated Aug. 17, 2010, filed Apr. 13, 2011 (9 pages).
Leo, "Competency and the Capacity to Make Treatment Decisions: A Primer for Primary Care Physicians," Primary Care Companion J_ Clin. Psychiatry, vol. 1, No. 5, Oct. 1999, pp. 131-141.
Letter of Acceptance for AU 2010202422, dated Oct. 7, 2010.
Letter of acceptance of AU application 2009202685, dated Aug. 10, 2010, 3 pages.
Lipschultz, "The effect of dexrazoxane on myocardial injury in doxorubicin-treated children with acute lymphoblastic leukemia," New England Journal of Medicine, vol. 351, pp. 145-153 (2004).
Lipschultz, "The incidence of pediatric cardiomyopathy in two regions of the United States," New England Journal of Medicine, Apr. 24, 2003. «http://www.nejm.org/doi/full/10.1056/NEJMoa021715», 348 (17): 1647-1655.
Lipshultz et al., "Cardiovascular status of infants and children of women infected with HIV-1 (P2C2 HIV): a cohort study," The Lancet, vol. 360, pp. 368-373 (2002).
Lipshultz et al., "Cardiovascular Trials in Long-Term Survivors of Childhood Cancer," Journal of Clinical Oncology, vol. 22, No. 5, pp. 769-773 (2004).
Lipshultz et al., "Long-Term Enalapril Therapy for Left Ventricular Dysfunction in Doxorubicin-Treated Survivors of Childhood Cancer," Journal of Clinical Oncology, vol. 20, No. 23, pp. 4517-4522 (2002).
Lipshultz, "Chronic Progressive Cardiac Dysfunction Years After Doxorubicin Therapy for Childhood Acute Lymphoblastic Leukemia," Journal of Clinical Oncology, vol. 23, No. 12, 8 pages (2005).
Lipshultz, "Clinical research directions in pediatric cardiology," Current Opinion in Pediatrics, vol. 21, pp. 585-593 (2009).
Lipshultz, "Establishing norms for echocardiographic measurement of cardiovascular structures and function in children," J_ Appl. Physiol., vol. 99, pp. 386-388 (2005).
Lipshultz, "Frequency of clinically unsuspected myocardial injury at a children's hospital," American Heart Journal, vol. 151, No. 4, pp. 916-922 (2006).
Lipshultz, "Ventricular dysfunction clinical research in infants, children and adolescents," Progress in Pediatric Cardiology, 2000, 12: 1-28.
Lipshultz. "Ventricular dysfunction clinical research in infants, children and adolescents," Progress in Pediatric Cardiology, vol. 12, pp. 1-28 (2000).
Loh et al., "Cardiovascular Effects of Inhaled Nitric Oxide in Patients with Left Ventricular Dysfunction," Circulation, 1994, 90: 2780-2785.
Lunn, "Subspecialty Clinics: Anesthesiology: Inhaled Nitric Oxide Therapy," Mayo Clin. Proc., 1995, 70: 247-255.
Macrae et al., "Inhaled Nitric Oxide Therapy in Neonates and Children: Reaching a European Consensus," Intensive Care Medicine, 2004, 30: 372-380.

(56) References Cited

OTHER PUBLICATIONS

Macrae, "Drug therapy in persistent pulmonary hypertension of the newborn," Semin. Neonatal, vol. 2, pp. 49-58 (1997).
Madriago et al., "Heart Failure in Infants and Children," Pediatrics in Review, vol. 31, pp. 4-12 (2010).
Magee et al., "Comparison of Supplemental Oxygen and Nitric Oxide for Inhalation plus oxygen in the evaluation of the reactivity of the pulmonary vasculature during Acute Pulmonary Vasodilator Testing," Oct. 1, 2004-Oct. 31, 2006, Research project description, 1 page, http://www.rbht.nhs.uk/research.
*Mallinckrodt Hosp. Prods. IP Ltd. v. Praxair Distrib., Inc.*, No. 15-170-GMS, Praxair's Opening Claim Construction Brief Regarding U.S. Pat. No. 8,846,112, filed on Mar. 17, 2016, 1-50.
*Mallinckrodt Hosp. Prods. IP Ltd. v. Praxair Distrib., Inc.*, No. 15-170-GMS, Praxair's Responsive Claim Construction Brief Regarding U.S. Pat. No. 8,846,112, filed on Apr. 14, 2016, 1-48.
*Mallinckrodt Hospital Products IP Ltd., INO Therapeutics LLC And Ikaria, Inc., v. Praxair Distribution, Inc., and Praxair, Inc.*, "Plaintiffs' Second Supplemental Objections and Responses to Praxair's Second Set of Interrogatories (No. 13).," C.A. No. 15-170 (GMS), dated Sep. 12, 2016, 31 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, "Defendants' Proposed Findings of Fact and Conclusions of Law," dated May 3, 2017, 58 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, "Expert Report of Alan H. Friedman, M.D.," dated Oct. 27, 2016, 82 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, "Judgment," dated Sep. 5, 2017, 2 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, "Memorandum," dated Sep. 5, 2017, 45 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, "Order," dated Sep. 5, 2017, 1 page.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, "Plaintiffs' Proposed Findings of Fact and Conclusions of Law," dated May 3, 2017, 54 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, "Proposed Joint Pretrial Order," dated Feb. 17, 2017, 13 pages (Redacted Version).
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Exhibit 1: Joint Statement of Uncontested Facts, dated Feb. 17, 2017, 12 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Exhibit 2.1: Plaintiffs' Statement of Contested Issues of Fact and Law, dated Feb. 17, 2017, 6 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Exhibit 2.2: Defendants' Statement of Contested Issues of Fact and Law, dated Feb. 17, 2017, 6 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, retrieved on Oct. 27, 2017, 47 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Trial Transcript: Day 1 of Bench Trial, dated Mar. 13, 2017, 102 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Trial Transcript: Day 2 of Bench Trial, dated Mar. 15, 2017, 103 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Trial Transcript: Day 3 of Bench Trial, dated Mar. 16, 2017, 97 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Trial Transcript: Day 4 of Bench Trial, dated Mar. 17, 2017, 107 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Trial Transcript: Day 5 of Bench Trial, dated Mar. 20, 2017, 93 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Trial Transcript: Day 6 of Bench Trial, dated Mar. 21, 2017, 87 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS, Trial Transcript: Day 7 of Bench Trial, dated Mar. 22, 2017, 36 pages.
*Mallinckrodt Hospital Products IP LTD., INO Therapeutics LLC, and Ikaria, Inc., v. Praxair Distribution, Inc. and Praxair, Inc.*, C.A. Case No. 1:15-cv-00170-GMS.: Deposition Transcript dated Jan. 5, 2017 Deposition of Geoffrey Lahn Rosenthal, M.D., 99 pages.
Malloy, "Nitric Oxide Weaning, RT: For Decision Makers in Respiratory Care," http://rtmagazine.com/issues/ articles/2000-12_05.asp, 3 pages, Dec. 2000.
Manktelow et al., "Physiologic Determinants of the Response to Inhaled Nitric Oxide in Patients with Acute Respiratory Distress Syndrome," Anesthesiology, 1997, 87: 297-307.
Martinez et al., "Dermatological Cryosurgery in Primary Care with Dimethyl Ether Propane Spray in Comparison with Liquid Nitrogen," Atnecion Primaria, vol. 18, No. 5, pp. 211 and 216 (1996).
Matsumoto et al., "Effect of Inhaled Nitric Oxide on Gas Exchange in Patients with Congestive Heart Failure," Annals of Internal Medicine, vol. 130, No. 1, pp. 40-44 (1999).
Matthews et al., "The Right Ventricular Failure Risk Score: A Pre-Operative Tool for Assessing the Risk of Right Ventricular Failure in Left Ventricular Assist Device Candidates," J. Am. Coll. Cardiol., Jun. 3, 2008, 51(22): 2163-2172.
McLaughlin et al., "Pulmonary Arterial Hypertension," Circulation, vol. 114, pp. 1417-1431 (2006).
McMullan et al., Alterations in Endogenous Nitric Oxide Production After Cardiopulmonary Bypass in Lambs with Normal and Increased Pulmonary Blood Flow; Circulation 102 [suppl 111]:III-172-III-178 (2000).
Medical Card System, Inc., "Inhaled Nitric Oxide (INO) In Neonates," Medical Policy: MP-ME-01-08, Aug. 25, 2008, 1-12.
Meyler's Side Effects of Drugs: The International Encyclopedia of Adverse Drug Reactions and Interactions, Nitric Oxide, Fifteenth Edition, Elsevier B.V. (2006).
Michelakis et al., "Oral Sildenafil Is an Effective and Specific Pulmonary Vasodilator in Patients with Pulmonary Arterial Hypertension: Comparison with Inhaled Nitric Oxide," Circulation vol. 105, pp. 2398-2403 (2002).
Miller et al., "Guidelines for the safe administration of inhaled nitric oxide," Archives of Disease in Childhood, vol. 10, pp. F47-F49 (1994).
Miller et al., "Nutrition in Pediatric Cardiomyopathy," Prag. Pediatr. Cardiol. vol. 24(1), pp. 59-71 (2007).
Mone, "Effects of Environmental Exposures on the Cardiovascular System: Prenatal Period Through Adolescence," Pediatrics. vol. 113, No. 4, pp. 1058-1069 (2004).
Morales-Blanhir et al., "Clinical value of vasodilator test with inhaled nitric oxide for predicting long-term response to oral vasodilators in pulmonary hypertension," Respiratory Medicine, vol. 98, pp. 225-234 (2004).
Morris et al., "Inhaled nitric oxide as a selective pulmonary vasodilator in clinical anesthesia," Journal of the American Association of Nurse Anesthetists, Feb. 1997, 65(1): 59-67.

(56) References Cited

OTHER PUBLICATIONS

Moss et al., "Moss and Adams' Heart Disease in Infants, Children, and Adolescents," Coarctation of the Aorta, vol. 1, p. 991 in part (2007).
Mourani et al., "Effects of Long-term Sildenafil Treatment for Pulmonary Hypertension in Infants with Chronic Lung Disease," J. Pediatr., Mar. 2009, 154(3): 379-384.
Mourani, et al., "Left Ventricular Diastolic Dysfunction in Bronchopulmonary Dysplasia," J. of Pediatrics, 152:291-293 (2008).
Murray et al., "Nitric Oxide and Septic Vascular Dysfunction," Anesth. Analg. vol. 90, pp. 89-101 (2000).
Murray, "Angiotensin Converting Enzyme Inhibitory Peptides Derived from Food Proteins: Biochemistry, Bioactivity and Production," Current Pharmaceutical Design, pp. 773-791 (2007).
Myers, "Therapeutic Gases for Neonatal and Pediatric Respiratory Care," Respiratory Care, Apr. 2003, 48(4): 399-425.
Nakagawa et al., "Dose response to inhaled nitric oxide in pediatric patients with pulmonary hypertension and acute respiratory distress syndrome," The Journal of Pediatrics, Jul. 1997, 131: 63-69.
Namachivayam et al., "Sildenafil Prevents Rebound Pulmonary Hypertension after Withdrawal of Nitric Oxide in Children," Am. J. Respir. Crit. Care Med., 2006, 174: 1042-1047.
National Pulmonary Hypertension Centres of the UK and Ireland, Consensus statement on the management of pulmonary hypertension in clinical practice in the UK and Ireland: Thorax, 2008, 63: (Suppl II):ii1-ii41.
Natori et al., "Inhaled Nitric Oxide Modifies Left Ventricular Diastolic Stress in the Presence of Vasoactive Agents in Heart Failure," Am. J_ Respir. Crit. Care Med, vol. 167, pp. 895-901 (2003).
NIH CC: Critical Care Services, http://www.cc.nih.gov/ccmd/clinical_services.html; retrieved Mar. 10, 2011, 3 pages.
NIH Clinical Center 2 Critical Care Medicine Department Sample Rotations, Updated Jan. 2007.
NIH Clinical Center 2 Critical Care Medicine Department Sample Rotations, Updated Jan. 2007 << http://www.cc.nih.gov/ccmd/prof_opps/rotation.html>>.
NIH Clinical Center Services, retrieved at <http://www.cc.nih.gov/ccmd/clinical_services.html» on Aug. 18, 2010.
NIH Clinical Center, Department Policy and Procedure Manual for the Critical Care Therapy and Respiratory Care Section; Nitric Oxide Therapy, sections 3.1-3.1.2 & 5.2.3 (2000).
Norman et al., "Criteria, Protocols And Reporting Forms For Initial Left Ventricular Assist Device Clinical Trials," Cardiovascular Diseases, Bulletin of the Texas Heart Institute, 1975, 2(3): 438-445.
Notification of Reason for Rejection, dated Jul. 30, 2010, from Japanese Patent Application No. 2009-157623 (cites foreign references).
Office Action for AU 2010202422 dated Jul. 9, 2010, 3 pages.
Office Action from AU 2009202685 dated Mar. 15, 2010.
Office Action from AU 2010206032 dated Aug. 16, 2010 (3 pages).
Office Action Response for AU 2009202685 dated Mar. 15, 2010 OA, filed Jun. 8, 2010 (16 pages).
Office Action Response for JP2007157623 filed on Nov. 12, 2009 (no English translation).
Office Action Response to AU 2010202422 OA dated Jul. 9, 2010, response filed Sep. 1, 2010.
Original INOT22 Protocol, Excerpt from prosecution history of U.S. Pat. No. 8,795,741 (submitted as Appendix 1 to Dr. Baldassarre Declaration under 37 C.F.R. § 1.131), pp. 1-58.
Oudiz et al., "Cardiac Catheterization in Pulmonary Arterial Hypertension: An Updated Guide to Proper Use," Retrieved from the Internet: URL<http://www.phaonlineuniv.org/Journal/Article.cfm?ItemNumber=645>, 2005, 4(3): 1-10.
Ovodov et al., "Nitric Oxide: Clinical Applications." Seminars in Anesthesia. Saunders. CO, New York,, NY, vol. 19, No. 2, pp. 88-97 (2000).
Patent Owner's Exhibit 2001 in IPR2015-00529: Supplemental Remarks filed May 9, 2012 in U.S. Appl. No. 12/821,020, 22 pages.
Patent Owner's Exhibit 2002 in IPR2015-00529: Non-Final Office Action dated Jan. 31, 2012, in U.S. Appl. No. 12/821,020, 23 pages.
Patent Owner's Exhibit 2014 in IPR2015-00529: Interview Summary dated Sep. 9, 2010 in U.S. Appl. No. 12/821,020 ('966 Patent), 4 pages.
Patent Owner's Exhibit 2019 in IPR2015-00529: Patent Owner's Updated Power of Attorney, dated Oct. 29, 2015, 3 pages.
Patent Owner's Exhibit 2020 in IPR2015-00529: Declaration of Geoffrey L. Rosenthal, M.D., Ph.D. in Support of Patent Owner's Response to Praxair's Petition for Inter Partes Review of U.S. Pat. No. 8,846,112, dated Nov. 5, 2015, 56 pages.
Patent Owner's Exhibit 2022 in IPR2015-00529: Deposition of Dr. Maurice Beghetti, dated Oct. 12, 2015, 283 pages.
Patent Owner's Exhibit 2035 in IPR2015-00529: Nitroglycerin in 5% Dextrose Injection Label, Oct. 2014, pp. 1-12.
Patent Owner's Exhibit 2036 in IPR2015-00529: Hearing Before the Board During the Deposition of Geoffrey L. Rosenthal, M.D., Ph.D., dated Jan. 5, 2016, pp. 1-14.
Pazopanib Plus Lapatinib Compared to Lapatinib Alone in Subjects With Inflammatory Breast Cancer, p. 4, ClinicalTrials.gov, «http://clinicaltrials.gov/cl2/show/NCT00558103» Apr. 22, 2010.
PCT/US2010/038652 Search Report dated Jul. 29, 2010, 16 pages.
Pepke-Zaba et al., "Inhaled nitric oxide as a cause of selective pulmonary vasodilation in pulmonary hypertension," The Lancet, vol. 338, pp. 1173-1174 (1991).
Petitioner's Exhibit 1033 in IPR2015-00522: Claim Chart for Claims 1-3, 5-9, 11, 13-17, 20, 22-25, and 28, pp. 1-35.
Petitioner's Exhibit 1034 in IPR2015-00522: Claim Chart for Claims 4, 10, 12, 18, 19, 21, 26, 27, and 29, pp. 1-4.
Petitioner's Exhibit 1035 in IPR2015-00522: Claim Chart for Claims 1-29, pp. 1-44.
Petitioner's Exhibit 1036 in IPR2015-00524: Claim Chart for Claims 1-3, 5-9, 11, 13-14, 16-18, 21, 23-27, and 29, pp. 1-36.
Petitioner's Exhibit 1037 in IPR2015-00524: Claim Chart for Claims 4, 10, 12, 15, 19, 20, 22, 28, and 30, pp. 1-4.
Petitioner's Exhibit 1038 in IPR2015-00524: Claim Chart for Claims 1-30, pp. 1-41.
Petitioner's Exhibit 1039 in IPR2015-00525: Claim Chart for Claims 1, 2, 4, 6, 7, 9, 11-13, 15, 18, 20, 21, 23, and 25, pp. 1-26.
Petitioner's Exhibit 1040 in IPR2015-00525: Claim Chart for Claims 3, 5, 8, 10, 14, 16, 17, 19, 22, and 24, pp. 1-4.
Petitioner's Exhibit 1041 in IPR2015-00525: Claim Chart for Claims 1-25, pp. 1-34.
Petitioner's Exhibit 1042 in IPR2015-00526: Claim Chart for Claims 1, 2, 4, 6-14, 17-23, 31-32, 34-35, 37-40, and 42-44, pp. 1-69.
Petitioner's Exhibit 1043 in IPR2015-00526: Claim Chart for Claims 3, 5, 15, 16, 36 and 41, pp. 1-3.
Petitioner's Exhibit 1044 in IPR2015-00526: Claim Chart for Claims 1-23, 31-32, and 34-44, pp. 1-100.
Petitioner's Exhibit 1045 in IPR2015-00526: Claim Chart for Claims 24-27, 29-30 and 33, pp. 1-17.
Petitioner's Exhibit 1046 in IPR2015-00526: Claim Chart for Claim 28, 1 page.
Petitioner's Exhibit 1047 in IPR2015-00526: Claim Chart for Claims 24-30 and 33, pp. 1-19.
Petitioner's Exhibit 1048 in IPR2015-00529: Claim Chart.
Petitioner's Exhibit 1051 in IPR2015-00526: Webster's Third New International Dictionary of the English Language Unabridged, 2002, 385-388.
Petitioner's Exhibit 1058 in IPR2015-00529: E-mails between B. Steinberg and B. Weed RE: Praxair/Ikaria-IPR2015-00529-PO Witness Deposition Scheduling, dated Dec. 14, 2015, Dec. 17, 2015, Dec. 18, 2015, and Dec. 30, 2015, 3 pages.
Pilbeam, Mechanical Ventilation, Special Techniques in Mechanical Ventilation, § 4: Nitric Oxide, 4th ed., 2006, 1-16.
Plaintiff's Opposition to Defendants' Motion for Judgment on the Pleadings for Counts I-V of Plaintiffs' Complaint, Case No. 2015-cv-00170, dated Jan. 27, 2016, 540 pages.
Pozzoli et al., "Non-invasive Estimation of Left Ventricular Filling Pressures by Doppler Echocardiography," Eur. J. Echocardiography, 2002, 3: 75-79.

(56) References Cited

OTHER PUBLICATIONS

*Praxair Distrib., Inc.* v. *INO Therapeutics, Inc.*, Decision Denying Institution of Inter Partes Review Nos. IPR2015-00522, -00524, -00525, -00526, dated Jul. 29, 2015, 25 pages.
*Praxair Distrib., Inc.* v. *INO Therapeutics, Inc.*, Petition for Inter Partes Review of U.S. Pat. No. 8,431,163, filed Jan. 5, 2015, 59 pages.
*Praxair Distribution, Inc. and NOxBOX Limited* v. *Mallinckrodt Hospital Products IP Ltd.*, IPR2016-00777, "Patent Owner's Exhibit List," dated Jun. 30, 2016, 6 pages.
*Praxair Distribution, Inc. and NOxBOX Limited* v. *Mallinckrodt Hospital Products IP Ltd.*, "Decision Denying Institution of Inter Partes Review for IPR2016-00777 (U.S. Pat. No. 8,282,966 B2); IPR2016-00778 (U.S. Pat. No. 8,431,163 B2); IPR2016-00779 (U.S. Pat. No. 8,293,284 B2); IPR2016-00780 (U.S. Pat. No. 8,795,741 B2)," dated Sep. 22, 2016, 13 pages.
*Praxair Distribution, Inc. and NOxBOX Limited* v. *Mallinckrodt Hospital Products IP Ltd., and INO Therapeutics, Inc. d/b/a Ikaria, Inc.*, IPR2016-00777, "Notice of Filing Date Accorded to Petition and Time for Filing Patent Owner Preliminary Response," dated Mar. 30, 2016, 5 pages.
*Praxair Distribution, Inc. and NOxBOX Limited* v. *Mallinckrodt Hospital Products IP Ltd., and INO Therapeutics, Inc. d/b/a Ikaria, Inc.*, IPR2016-00777, "Petition for Inter Partes Review of U.S. Pat. No. 8,282,966," dated Mar. 23, 2016, 59 pages.
*Praxair Distribution, Inc. and NOxBOX Limited* v. *Mallinckrodt Hospital Products IP Ltd., and INO Therapeutics, Inc. d/b/a Ikaria, Inc.*, IPR2016-00778, "Notice of Filing Date Accorded to Petition and Time for Filing Patent Owner Preliminary Response," dated Mar. 30, 2016, 5 pages.
*Praxair Distribution, Inc. and NOxBOX Limited* v. *Mallinckrodt Hospital Products IP Ltd., and INO Therapeutics, Inc. d/b/a Ikaria, Inc.*, IPR2016-00778, "NOxBOX Limited's Power of Attorney for Inter Partes Review of U.S. Pat. No. 8,28,966; U.S. Pat. No. 8,293,284; U.S. Pat. No. 8,431,163; U.S. Pat. No. 8,795,741; and U.S. Pat. No. 8,846,112," dated Mar. 18, 2016, 3 pages.
*Praxair Distribution, Inc. and NOxBOX Limited* v. *Mallinckrodt Hospital Products IP Ltd., and INO Therapeutics, Inc. d/b/a Ikaria, Inc.*, IPR2016-00778, "NOxBOX Limited's Power of Attorney for Inter Partes Review of U.S. Pat. No. 8,28,966; U.S. Pat. No. 8,293,284; U.S. Pat. No. 8,431,163; U.S. Pat. No. 8,795,741; and U.S. Pat. No. 8,846,112," dated Mar. 23, 2016, 4 pages.
*Praxair Distribution, Inc. and NOxBOX Limited* v. *Mallinckrodt Hospital Products IP Ltd., and INO Therapeutics, Inc. d/b/a Ikaria, Inc.*, IPR2016-00778, "Petition for Inter Partes Review of U.S. Pat. No. 8,431,163," dated Mar. 23, 2016, 59 pages.
*Praxair Distribution, Inc. and NOxBOX Limited* v. *Mallinckrodt Hospital Products IP Ltd., and INO Therapeutics, Inc. d/b/a Ikaria, Inc.*, IPR2016-00778, "Praxair Distribution, Inc.'s Power of Attorney for Inter Partes Review of U.S. Pat. No. 8,282,966; U.S. Pat. No. 8,293,284; U.S. Pat. No. 8,431,163; U.S. Pat. No. 8,795,741; and U.S. Pat. No. 8,846,112," dated Mar. 22, 2016, 4 pages.
*Praxair Distribution, Inc. and NOxBOX Limited* v. *Mallinckrodt Hospital Products IP Ltd., and INO Therapeutics, Inc. d/b/a Ikaria, Inc.*, IPR2016-00779, "Notice of Filing Date Accorded to Petition and Time for Filing Patent Owner Preliminary Response," dated Mar. 30, 2016, 5 pages.
*Praxair Distribution, Inc. and NOxBOX Limited* v. *Mallinckrodt Hospital Products IP Ltd., and INO Therapeutics, Inc. d/b/a Ikaria, Inc.*, IPR2016-00779, "Petition for Inter Partes Review of U.S. Pat. No. 8,293,284," dated Mar. 23, 2016, 60 pages.
*Praxair Distribution, Inc. and NOxBOX Limited* v. *Mallinckrodt Hospital Products IP Ltd., and INO Therapeutics, Inc. d/b/a Ikaria, Inc.*, IPR2016-00780, "Notice of Filing Date Accorded to Petition and Time for Filing Patent Owner Preliminary Response," dated Apr. 5, 2016, 5 pages.
*Praxair Distribution, Inc. and NOxBOX Limited* v. *Mallinckrodt Hospital Products IP Ltd., and INO Therapeutics, Inc. d/b/a Ikaria, Inc.*, IPR2016-00780, "Petition for Inter Partes Review of U.S. Pat. No. 8,795,741," dated Mar. 23, 2016, 62 pages.

*Praxair Distribution, Inc. and NOxBOX Limited* v. *Mallinckrodt Hospital Products IP Ltd., and INO Therapeutics, Inc. d/b/a Ikaria, Inc.*, IPR2016-00781, "Notice of Filing Date Accorded to Petition and Time for Filing Patent Owner Preliminary Response," dated Apr. 5, 2016, 5 pages.
*Praxair Distribution, Inc. and NOxBOX Limited* v. *Mallinckrodt Hospital Products IP Ltd., and INO Therapeutics, Inc. d/b/a Ikaria, Inc.*, IPR2016-00781, "Petition for Inter Partes Review of U.S. Pat. No. 8,846,112," dated Mar. 23, 2016, 62 pages.
*Praxair Distribution, Inc. and NOxBOX Limited* v. *Mallinckrodt Hospital Products IP Ltd.*, IPR2016-00777, "Patent Owner's Mandatory Notices," dated Apr. 13, 2016, 8 pages.
*Praxair Distribution, Inc. and NOxBOX Limited* v. *Mallinckrodt Hospital Products IP Ltd.*, IPR2016-00777, "Patent Owner's Preliminary Response," dated Jun. 30, 2016, 70 pages.
*Praxair Distribution, Inc. and NOxBOX Limited* v. *Mallinckrodt Hospital Products IP Ltd.*, IPR2016-00778, "Patent Owner's Exhibit List," dated Jun. 30, 2016, 6 pages.
*Praxair Distribution, Inc. and NOxBOX Limited* v. *Mallinckrodt Hospital Products IP Ltd.*, IPR2016-00778, "Patent Owner's Mandatory Notices," dated Apr. 13, 2016, 8 pages.
*Praxair Distribution, Inc. and NOxBOX Limited* v. *Mallinckrodt Hospital Products IP Ltd.*, IPR2016-00778, "Patent Owner's Preliminary Response," dated Jun. 30, 2016, 70 pages.
*Praxair Distribution, Inc. and NOxBOX Limited* v. *Mallinckrodt Hospital Products IP Ltd.*, IPR2016-00779, "BPAI Routing Sheet," dated Sep. 22, 2016, 1 page.
*Praxair Distribution, Inc. and NOxBOX Limited* v. *Mallinckrodt Hospital Products IP Ltd.*, IPR2016-00779, "Patent Owner's Exhibit List," dated Jun. 30, 2016, 6 pages.
*Praxair Distribution, Inc. and NOxBOX Limited* v. *Mallinckrodt Hospital Products IP Ltd.*, IPR2016-00779, "Patent Owner's Mandatory Notices," dated Apr. 13, 2016, 8 pages.
*Praxair Distribution, Inc. and NOxBOX Limited* v. *Mallinckrodt Hospital Products IP Ltd.*, IPR2016-00779, "Patent Owner's Preliminary Response," dated Jun. 30, 2016, 69 pages.
*Praxair Distribution, Inc. and NOxBOX Limited* v. *Mallinckrodt Hospital Products IP Ltd.*, IPR2016-00780, "Patent Owner's Exhibit List," dated Jun. 30, 2016, 6 pages.
*Praxair Distribution, Inc. and NOxBOX Limited* v. *Mallinckrodt Hospital Products IP Ltd.*, IPR2016-00780, "Patent Owner's Mandatory Notices," dated Apr. 13, 2016, 8 pages.
*Praxair Distribution, Inc. and NOxBOX Limited* v. *Mallinckrodt Hospital Products IP Ltd.*, IPR2016-00780, "Patent Owner's Preliminary Response," dated Jun. 30, 2016, 69 pages.
*Praxair Distribution, Inc. and NOxBOX Limited* v. *Mallinckrodt Hospital Products IP Ltd.*, IPR2016-00781, "Patent Owner's Mandatory Notices," dated Apr. 13, 2016, 8 pages.
*Praxair Distribution, Inc. and NOxBOX Limited* v. *Mallinckrodt Hospital Products IP Ltd.*, IPR2016-00781, "Patent Owner's Exhibit List," dated Jun. 6, 2016, 6 pages.
*Praxair Distribution, Inc. and NOxBOX Limited* v. *Mallinckrodt Hospital Products IP Ltd.*, IPR2016-00781, "Patent Owner's Preliminary Response," dated Jun. 6, 2016, 71 pages.
*Praxair Distribution, Inc. and Praxair Inc.* v. *Mallinckrodt Hospital Products IP Ltd.*, IPR2015-00522, "Notice of Refund," dated May 11, 2016, 2 pages.
*Praxair Distribution, Inc. and Praxair Inc.* v. *Mallinckrodt Hospital Products IP Ltd.*, IPR2015-00522, "Request for Refund of Post-Institution Fees," dated May 9, 2016, 4 pages.
*Praxair Distribution, Inc. and Praxair, Inc.* v. *INO Therapeutics LLC and Ikaria, Inc.*, IPR2015-00529, "Petitioner's Notice of Deposition of Geoffrey Rosenthal, M.D., Ph.D.," dated Dec. 26, 2015, 3 pages.
*Praxair Distribution, Inc. and Praxair, Inc.* v. *INO Therapeutics LLC and Ikaria, Inc.*, IPR2015-00529, "Petitioner's Reply to Patent Owner's Response to Petition," dated Jan. 15, 2015, 28 pages.
*Praxair Distribution, Inc. and Praxair, Inc.* v. *INO Therapeutics LLC and Ikaria, Inc.*, IPR2015-00529, "Petitioner's Updated Exhibit List," dated Jan. 15, 2015, 8 pages.
*Praxair Distribution, Inc. and Praxair, Inc.* v. *INO Therapeutics, LLC and Ikaria, Inc.*, IPR2015-00525, "Notice of Filing Date

(56) References Cited

OTHER PUBLICATIONS

Accorded to Petition and Time for Filing Patent Owner Preliminary Response," dated Feb. 6, 2015, 3 pages.
*Praxair Distribution, Inc. and Praxair, Inc. v. INO Therapeutics, LLC and Ikaria, Inc.*, IPR2015-00526, "Petitioner's Updated Mandatory Notices," dated Feb. 25, 2015, 4 pages.
*Praxair Distribution, Inc. and Praxair, Inc. v. INO Therapeutics, LLC and Ikaria, Inc.*, PR2015-00526, "Notice of Filing Date Accorded to Petition and Time for Filing Patent Owner Preliminary Response," dated Feb. 6, 2015, 3 pages.
*Praxair Distribution, Inc. and Praxair, Inc. v. Mallinckrodt Hospital Products IP Ltd.*, IPR2015-00525, "Notice of Refund," dated May 11, 2016, 2 pages.
*Praxair Distribution, Inc. and Praxair, Inc. v. Mallinckrodt Hospital Products IP Ltd.*, IPR2015-00525, "Request for Refund of Post-Institution Fees," dated May 9, 2016, 4 pages.
*Praxair Distribution, Inc. and Praxair, Inc. v. Mallinckrodt Hospital Products IP Ltd.*, IPR2015-00526, "Notice of Refund," dated May 11, 2016, 2 pages.
*Praxair Distribution, Inc. and Praxair, Inc. v. Mallinckrodt Hospital Products IP Ltd.*, IPR2015-00526, "Request for Refund of Post-Institution Fees," dated May 9, 2016, 4 pages.
*Praxair Distribution, Inc. and Praxair, Inc., v. INO Therapeutics LLC, and Ikaria, Inc.*, IPR 2015-00524, "Notice of Filing Date Accorded to Petition and Time for Filing Patent Owner Preliminary Response," dated Feb. 4, 2015, 3 pages.
*Praxair Distribution, Inc. and Praxair, Inc., v. INO Therapeutics LLC, and Ikaria, Inc.*, IPR 2015-00524, "Petitioner's Updated Mandatory Notices," dated Feb. 25, 2015, 4 pages.
*Praxair Distribution, Inc. and Praxair, Inc., v. INO Therapeutics, LLC and Ikaria, Inc.*, IPR2015-00529, "Notice of Filing Date Accorded to Petition and Time for Filing Patent Owner Preliminary Response," dated Feb. 6, 2015, 3 pages.
*Praxair Distribution, Inc. and Praxair, Inc., v. Mallinckrodt Hospital Products IP Ltd.*, IPR 2015-00524, "Notice of Refund," dated May 11, 2016, 2 pages.
*Praxair Distribution, Inc. and Praxair, Inc., v. Mallinckrodt Hospital Products IP Ltd.*, IPR 2015-00524, "Request for Refund of Post-Institution Fees," dated May 9, 2016, 4 pages.
*Praxair Distribution, Inc. v. INO Therapeutics LLC*, IPR2015-00525, "INO Therapeutics LLC Mandatory Notices," dated Jan. 26, 2015, 5 pages.
*Praxair Distribution, Inc. v. INO Therapeutics LLC*, IPR2015-00525, "Patent Owner's Amended Mandatory Notice," dated Feb. 25, 2015, 4 pages.
*Praxair Distribution, Inc. v. INO Therapeutics LLC*, IPR2015-00525, "Patent Owner's Amended Mandatory Notice," dated May 7, 2015, 4 pages.
*Praxair Distribution, Inc. v. INO Therapeutics LLC*, IPR2015-00525, "Preliminary Response by Patent Owner," dated May 6, 2015, 74 pages.
*Praxair Distribution, Inc. v. INO Therapeutics LLC*, IPR2015-00526, "INO Therapeutics LLC Mandatory Notices," dated Jan. 26, 2015, 5 pages.
*Praxair Distribution, Inc. v. INO Therapeutics LLC*, IPR2015-00526, "Patent Owner's Amended Mandatory Notice," dated Feb. 25, 2015, 4 pages.
*Praxair Distribution, Inc. v. INO Therapeutics LLC*, IPR2015-00526, "Patent Owner's Amended Mandatory Notice," dated May 7, 2015, 4 pages.
*Praxair Distribution, Inc. v. INO Therapeutics LLC*, IPR2015-00526, "Patent Owner's Exhibit List," dated May 6, 2016, 5 pages.
*Praxair Distribution, Inc. v. INO Therapeutics LLC*, IPR2015-00526, "Preliminary Response by Patent Owner," dated May 6, 2015, 73 pages.
*Praxair Distribution, Inc. v. INO Therapeutics LLC*, IPR2015-00529, "Case Management and Scheduling Order," dated Jul. 30, 2015, 7 pages.
*Praxair Distribution, Inc. v. INO Therapeutics LLC*, IPR2015-00529, "Decision of Institution of Inter Partes Review," dated Jul. 29, 2015, 26 pages.
*Praxair Distribution, Inc. v. INO Therapeutics LLC*, IPR2015-00529, "Decision: Patent Owner's Motion for Withdrawal and Substitution of Counsel," dated Oct. 30, 2015, 3 pages.
*Praxair Distribution, Inc. v. INO Therapeutics LLC*, IPR2015-00529, "Ino Therapeutics LLC Mandatory Notices," dated Jan. 26, 2015, 5 pages.
*Praxair Distribution, Inc. v. INO Therapeutics LLC*, IPR2015-00529, "Notice of Stipulation to Modify the Scheduling Order," dated Oct. 29, 2015, 4 pages.
*Praxair Distribution, Inc. v. INO Therapeutics LLC*, IPR2015-00529, "Order Conduct of the Proceeding," dated Dec. 22, 2015, 4 pages.
*Praxair Distribution, Inc. v. INO Therapeutics LLC*, IPR2015-00529, "Order Conduct of the Proceeding," dated Sep. 17, 2015, 5 pages.
*Praxair Distribution, Inc. v. INO Therapeutics LLC*, IPR2015-00529, "Order: Requests for Oral Argument," dated Feb. 24, 2016, 4 pages.
*Praxair Distribution, Inc. v. INO Therapeutics LLC*, IPR2015-00529, "Order: Requests for Oral Argument," dated Mar. 22, 2016, 4 pages.
*Praxair Distribution, Inc. v. INO Therapeutics LLC*, IPR2015-00529, "Patent Owner INO Therapeutics LLC's Response to Praxair Distribution Inc's Petition for Inter Partes Review of U.S. Pat. No. 8,846,112," dated Nov. 5, 2015, 65 pages.
*Praxair Distribution, Inc. v. INO Therapeutics LLC*, IPR2015-00529, "Patent Owner's Amended Mandatory Notice," dated Feb. 25, 2015, 4 pages.
*Praxair Distribution, Inc. v. INO Therapeutics LLC*, IPR2015-00529, "Patent Owner's Amended Mandatory Notice," dated May 7, 2015, 4 pages.
*Praxair Distribution, Inc. v. INO Therapeutics LLC*, IPR2015-00529, "Patent Owner's Exhibit List," dated May 6, 2015, 6 pages.
*Praxair Distribution, Inc. v. INO Therapeutics LLC*, IPR2015-00529, "Patent Owner's Notice of Deposition of Dr. Maurice Beghetti," dated Sep. 28, 2015, 3 pages.
*Praxair Distribution, Inc. v. INO Therapeutics LLC*, IPR2015-00529, "Patent Owner's Updated Exhibit List," dated Nov. 5, 2015, 6 pages.
*Praxair Distribution, Inc. v. INO Therapeutics LLC*, IPR2015-00529, "Patent Owner's Updated Mandatory Notice," dated Dec. 4, 2015, 4 pages.
*Praxair Distribution, Inc. v. INO Therapeutics LLC*, IPR2015-00529, "Patent Owner's Updated Mandatory Notice," dated Nov. 3, 2015, 4 pages.
*Praxair Distribution, Inc. v. INO Therapeutics LLC*, IPR2015-00529, "Patent Owner's Updated Mandatory Notices," dated Feb. 10, 2016, 5 pages.
*Praxair Distribution, Inc. v. INO Therapeutics LLC*, IPR2015-00529, "Petitioner Praxair Distribution Inc.'s Objections to Patent Owner INO Therapeutics, LLC's Evidence," dated Nov. 13, 2015, 4 pages.
*Praxair Distribution, Inc. v. INO Therapeutics LLC*, IPR2015-00529, "Preliminary Response by Patent Owner," dated May 6, 2015, 66 pages.
*Praxair Distribution, Inc. v. INO Therapeutics LLC*, IPT2015-00525, "Patent Owner's Exhibit List," dated May 6, 2015, 6 pages.
*Praxair Distribution, Inc. v. INO Therapeutics, Inc. and Ikaria, Inc.*, IPR2015-00522, "Notice of Filing Date Accorded to Petition and Time for Filing Patent Owner Preliminary Response," dated Feb. 4, 2015, 3 pages.
*Praxair Distribution, Inc. v. INO Therapeutics, Inc. and Ikaria, Inc.*, IPR2015-00522, "Petitioner's Updated Mandatory Notices," dated Feb. 25, 2015, 4 pages.
*Praxair Distribution, Inc. v. INO Therapeutics, Inc. d/b/a Ikaria, Inc.*, IPR2015-00526, "Petition for Inter Partes Review of U.S. Pat. No. 8,795,741," dated Jan. 5, 2015, 72 pages.
*Praxair Distribution, Inc. v. INO Therapeutics, Inc. d/b/a Ikaria, Inc.*, IPR2015-0529, Petition for Inter Partes Review of U.S. Pat. No. 8,846,112, dated Jan. 5, 2015, 72 pages.

(56) References Cited

OTHER PUBLICATIONS

*Praxair Distribution, Inc. v. INO Therapeutics, Inc. d/b/a/ Ikaria, Inc.*, IPR2015-00522, "Petition for Inter Partes Review of U.S. Pat. No. 8,282,966," dated Jan. 5, 2015, 70 pages.
*Praxair Distribution, Inc. v. INO Therapeutics, Inc.*, "Decision: Denying Institution of Inter Partes Review for IPR2015-00522 (U.S. Pat. No. 8,282,966 B2); IPR2015-00524 (U.S. Pat. No. 8,293,284 B2); IPR2015-00525 (U.S. Pat. No. 8,431,163 B2); IPR2015-00526 (U.S. Pat. No. 8,795,741 B2)," dated Jul. 29, 2015, 25 pages.
*Praxair Distribution, Inc. v. INO Therapeutics, Inc.*, IPR2015-00522, "INO Therapeutics LLC Mandatory Notices in an Inter Partes Review of U.S. Pat. No. 8,282,966," dated Jan. 26, 2015, 5 pages.
*Praxair Distribution, Inc. v. INO Therapeutics, Inc.*, IPR2015-00522, "Patent Owner's Amended Mandatory Notice," dated Feb. 25, 2015, 4 pages.
*Praxair Distribution, Inc. v. INO Therapeutics, Inc.*, IPR2015-00522, "Patent Owner's Amended Mandatory Notice," dated May 7, 2015, 4 pages.
*Praxair Distribution, Inc. v. INO Therapeutics, Inc.*, IPR2015-00522, "Patent Owner's Exhibit List," dated May 4, 2015, 5 pages.
*Praxair Distribution, Inc. v. INO Therapeutics, Inc.*, IPR2015-00522, "Preliminary Response by Patent Owners," dated May 4, 2015, 71 pages.
*Praxair Distribution, Inc. v. Mallinckrodt Hospital Products IP LTD.*, decision on appeals from USPTO Ptab No. IPR2015-00529; 2016-2616, 2016-2656 (Fed. Cir. May 16, 2018), pp. 1-21, and opinion concurring in the judgement, pp. 1-9.
*Praxair Distribution, Inc. v. Mallinckrodt Hospital Products IP LTD.*, IPR2015-00529, "Confirmation of Change of Patent Ownership Filed in Feb. 10, 2016 Updated Mandatory Notices," dated Jun. 20, 2016, 3 pages.
*Praxair Distribution, Inc. v. Mallinckrodt Hospital Products IP LTD.*, IPR2015-00529, "Final Written Decision," dated Jul. 7, 2016, 47 pages.
*Praxair Distribution, Inc. v. Mallinckrodt Hospital Products IP LTD.*, IPR2015-00529, "Oral Argument Transcript, Oral Argument Held Mar. 29, 2016," 66 pages.
*Praxair Distribution, Inc. v. Mallinckrodt Hospital Products IP LTD.*, IPR2015-00529, "Patent Owner's Notice of Cross-Appeal," dated Sep. 16, 2016, 52 pages.
*Praxair Distribution, Inc. v. Mallinckrodt Hospital Products IP LTD.*, IPR2015-00529, "Patent Owner's Objections to Petitioner's Demonstratives," dated Mar. 24, 2016, 5 pages.
*Praxair Distribution, Inc. v. Mallinckrodt Hospital Products IP LTD.*, IPR2015-00529, "Patent Owner's Request for Oral Argument," dated Feb. 22, 2016, 3 pages.
*Praxair Distribution, Inc. v. Mallinckrodt Hospital Products IP LTD.*, IPR2015-00529, Patent Owner's Sur-Reply to Praxair Distribution, Inc.'s Petition for Inter Partes Review of U.S. Pat. No. 8,846,112, dated Feb. 10, 2016, 13 pages.
*Praxair Distribution, Inc. v. Mallinckrodt Hospital Products IP LTD.*, IPR2015-00529, "Patent Owner's Transmittal Letter Accompanying Submission of Exhibit 2036," dated Mar. 30, 2016, 3 pages.
*Praxair Distribution, Inc. v. Mallinckrodt Hospital Products IP LTD.*, IPR2015-00529, "Patent Owner's Updated Exhibit List," dated Mar. 30, 2016, 6 pages.
*Praxair Distribution, Inc. v. Mallinckrodt Hospital Products IP LTD.*, IPR2015-00529, "Petitioner's Notice of Appeal," dated Sep. 6, 2016, 4 pages.
*Praxair Distribution, Inc. v. Mallinckrodt Hospital Products IP LTD.*, IPR2015-00529, "Petitioner's Objections to Patent Owner's Demonstrative Exhibits," dated Mar. 24, 2016, 3 pages.
*Praxair Distribution, Inc. v. Mallinckrodt Hospital Products IP LTD.*, IPR2015-00529, "Petitioner's Request for Oral Argument," dated Feb. 22, 2016, 4 pages.
*Praxair Distribution, Inc. v. Mallinckrodt Hospital Products IP LTD.*, IPR2015-00529, "Petitioner's Updated Mandatory Notices," dated Jul. 5, 2016, 3 pages.
*Praxair Distribution, Inc. v. Mallinckrodt Hospital Products IP LTD.*, IPR2015-00529, "Petitioner's Updated Mandatory Notices," dated Mar. 4, 2016, 4 pages.
*Praxair Distribution, Inc., and Praxair, Inc. v. INO Therapeutics, LLC and Ikaria, Inc.*, "Petitioner's Updated Mandatory Notices," dated Feb. 25, 2015, 4 pages.
*Praxair Distribution, Inc., v. INO Therapeutics LLC*, IPR 2015-00524, "INO Therapeutics LLC Mandatory Notices," dated Jan. 26, 2015, 5 pages.
*Praxair Distribution, Inc., v. INO Therapeutics LLC*, IPR 2015-00524, "Patent Owner's Amended Mandatory Notice," dated Feb. 25, 2015, 4 pages.
*Praxair Distribution, Inc., v. INO Therapeutics LLC*, IPR 2015-00524, "Patent Owner's Amended Mandatory Notice," dated May 7, 2015, 4 pages.
*Praxair Distribution, Inc., v. INO Therapeutics LLC*, IPR 2015-00524, "Patent Owner's Exhibit List," dated May 4, 2015, 5 pages.
*Praxair Distribution, Inc., v. INO Therapeutics LLC*, IPR 2015-00524, "Preliminary Response by Patent Owners," dated May 4, 2015, 69 pages.
*Praxair Distribution, Inc., v. INO Therapeutics, Inc. d/b/a Ikaria, Inc.*, IPR 2015-00524, "Petition for Inter Partes Review of U.S. Pat. No. 8,293,284," dated Jan. 5, 2015, 68 pages.
*Praxair Distribution, Inc., v. INO Therapeutics, Inc. d/b/a Ikaria, Inc.*, IPR2015-00525, "Petition for Inter Partes Review of U.S. Pat. No. 8,431,163," dated Jan. 5, 2015, 59 pages.
Praxair, Inc. Protest filed against CA2,671,029 on Jun. 2, 2014 (38 pages).
Preston et al.; Pulmonary Edema Caused by Inhaled Nitric Oxide therapy in Two Patients with Pulmonary Hypertension Associated with the CREST Syndrome; Chest 121:656-659 (2002).
Prior art notice issued in CA267102 on Aug. 9, 2013 (51 pages).
Rabkin et al., "Nitric Oxide for the Treatment of Post pneumonectomy Pulmonary Edema," Ann. Thorac. Surg., 2001, 72: 272-4.
Ratnasamy et al., "Associations between neurohormonal and inflammatory activation and heart failure in children," American Heart Journal, pp. 527-533 (2008).
Resolucion De Autorizacion De Comercializacion Del Medicamento Vasokinox 450 ppm mol/mol, gas para inhalacion en cilindro, n 69773, dated May 5, 2008, 39 pages (with English translation).
Response filed Aug. 18, 2010 to EP Search Report dated May 10, 10 for EP09251949.
Review of Parveen Khilnani, Practical Approach to Pediatric Intensive Care, Retrieved from the Internet: URL<www.archdischild.com>, 2005, p. 280.
Ricciardi et al., "Inhaled Nitric Oxide in Primary Pulmonary Hypertension: A Safe and Effective Agent for Predicting Response to Nifedipine," Journal of the American College of Cardiology (JACC,) vol. 32, No. 4, pp. 1068-1073 (1998).
Rich et al., "Inhaled Nitric Oxide for Cardiac Disease," Respir. Care, 1999, 44(2): 196-202.
Rimensberger et al., "Inhaled nitric oxide versus aerosolized iloprost in secondary pulmonary hypertension in children with congenital heart disease: vasodilator capacity and cellular mechanisms", Circulation, 2001, 103: 544-48.
Roberts et al., "Inhaled Nitric Oxide in Congenital Heart Disease," Circulation, 1993, 87(2): 447-453.
Roberts, "Inhaled Nitric Oxide and Persistent Pulmonary Hypertension of the Newborn," The New England Journal of Medicine, vol. 336, No. 9, pp. 605-610 (1997).
Roberts, "Nitric Oxide and the Lung," Marcel Dekker, Inc., New York, NY, pp. 333-363 (1997).
Roofthooft et al., "Persistent Pulmonary Hypertension of the Newborn with Transposition of the Great Arteries," Ann. Thorac. Surg., 2007, 83: 1446-50.
Rosales et al., "Adverse hemodynamic effects observed with inhaled nitric oxide after surgical repair of total anomalous pulmonary venous return," Pediatr. Cardiol., 1999, 20:224-26.
Rosenberg, "Inhaled nitric oxide in the premature infant with severe hypoxemic respiratory failure: A time for caution," The Journal of Pediatrics, vol. 133, Issue 6, pp. 720-722 (1998).
Rosenzweig et al., "Pulmonary arterial hypertension in children," Pediatr. Pulmonol., 2004, 38: 2-22.

(56) References Cited

OTHER PUBLICATIONS

Royster et al., "Differences in Pulmonary Artery Wedge Pressures Obtained by Balloon Inflation Versus Impaction Techniques," Anesthesiology, 1984, 61: 339-341.
Rubanyi, "Pathophysiology and Clinical Applications of Nitric Oxide," Harwood Academic Publishers, Endothelial Cell Research Series, Part B, 1989, 9 pages.
Rubin et al., "Evaluation and Management of the Patient with Pulmonary Arterial Hypertension," Ann. Intern. Med., 2005, 143: 282-292.
Russell et al., "The Effects of Inhaled Nitric Oxide on Postoperative Pulmonary Hypertension in Infants and Children Undergoing Surgical Repair of Congenital Heart Disease," Anesthesia & Analgesia, Jul. 1998, 87(1): 46-51.
S&P Capital IQ, Praxair Distribution, Inc., Private Company Profile, created Apr. 13, 2016, 1 page.
Sadiq et al., "Inhaled Nitric Oxide in the Treatment of Moderate Persistent Pulmonary Hypertension of the Newborn: A Randomized Controlled. Multicenter Trial." Journal of Perinatology, vol. 23, pp. 98-103 (2003).
Sample, "Technology today: Left ventricular assist devices," Retrieved from the Internet: URL<http://www.modernmedicine.com/modern-medicine/content/technology-today-left-ventricle.,.>, Nov. 2005, 6 pages.
Schannwell et al., "Diagnostics in Pulmonary Hypertension," Journal of Physiology and Pharmacology, 2007, 58(Suppl 5): 591-602.
Scherrer et al., "Inhaled Nitric Oxide for High-Altitude Pulmonary Edema," Ne J. Med., Mar. 7, Mar. 7, 1996, 334(10): 624-629.
Schreiber et al., "Inhaled Nitric Oxide in Premature Infants with the Respiratory Distress Syndrome," N. Engl. J. Med., 2003, 349: 2099-107.
Search Report from EP 09251949 dated May 10, 2010.
Sehgal et al., "Experience with Inhaled Nitric Oxide Therapy in Hypoxic Respiratory Failure of the Newborn," Indian J_ Chest Dis. Allied. Sci., vol. 47, pp. 245-249 (2005).
Sekar, "Inhaled nitric oxide in term and preterm infants," Journal of Perinatology, 2006, 26: S4-S7.
Semigran et al., "Hemodynamic Effects of Inhaled Nitric Oxide in Heart Failure," Journal of American College of Cardiology (JACC), vol. 24, No. 4, pp. 982-988 (1994).
Senni et al., "Heart Failure With Preserved Systolic Function: A Different Natural History?," Journal of the American College of Cardiology, 2001, 38(5): 1277-1282.
Shah et al., "Nitric Oxide Treatment for Pulmonary Hypertension After Neonatal Cardiac Operation," Ann. Thorac. Surg., 1995, 1791-1793.
Shapiro et al., "Diagnostic Dilemmas: Diastolic Heart Failure Causing Pulmonary Hypertension and Pulmonary Hypertension Causing Diastolic Dysfunction," Advances in Pulmonary Hypertension, vol. 5(1), pp. 13-20 (2006) http://www.phaonlineuniv.org/sites/default/files/spr_2006.pdf.
Shiel, "Morbid Anatomical Changes in the Lungs of Dogs after Inhalation of Higher Oxides of Nitrogen During Anaesthesia"; Brit. J_Anaesth. 39:413-424 (1967).
Sibutramine-melformin Combination vs. Sibutramine and Melformin Monotherapy in Obese Patients, p. 3, ClinicalTrials.gov, «http://clinicaltrials.gov/ct2/showNCT00941382> Sponsored by Laboratorios Silanes S.A. de C.V. and Jorge Gonzalez Canudas, Jul. 15, 2009.
Simonneau et al., "Clinical Classification of Pulmonary Hypertension," J. Am. Coll. Cardiol., 2004, 43(12 Suppl S): 5S-12S.
Simonneau et al., "Updated Clinical Classification of Pulmonary Hypertension," J. Am. Coll. Cardiol., 2009, 54(1 Suppl): S43-54.
Simonneau et al., "Updated Clinical Classification of Pulmonary Hypertension," J. Am. Coll. Cardiol., 2013, 62(25 Suppl): D34-41.
Singh et al., "Nitric Oxide, the biological mediator of the decade: fact or fiction?," Eur. Respir. J_ , vol. 10, pp. 699-707 (1997).
Smyth, "Inhaled nitric oxide treatment for preterm infants with hypoxic respiratory failure," Thorax, 55(Suppl 1):S51-S55 (2000).
Somarriba et al., "Exercise rehabilitation in pediatric cardiomyopathy," Progress in Pediatric Cardiology, vol. 25, pp. 91-102 (2008).
Soto et al., "Cardiopulmonary Hemodynamics in Pulmonary Hypertension: Pressure Tracings, Waveforms, and More," Advances in Pulmonary Hypertension Winter, vol. 7(4), pp. 386-393 (2008).
Stedman's Medical Dictionary at a Glance, 28th Ed, Lippincott Williams & Wilkins © 2006, p. 359.
Steinhorn et al., "Inhaled nitric oxide enhances oxygenation but not survival in infants with alveolar capillary dysplasia," The Journal of Pediatrics, pp. 417-422 (1997).
Steinhorn, "Persistent Pulmonary Hypertension in the Newborn and Infant," vol. 1(2), pp. 287-299 (1987) [downloadedfrom www.Emedicine.com on Jun. 10, 2008.
Steinhorn, "Pulmonary Hypertension, Persistent-Newborn," Updated Apr. 19, 2007, http://emedicine.medscape.com/ article/898437-overview.
Steudel et al., "Inhaled nitric oxide," Anesthesiology, vol. 91, pp. 1090-1121 (1999).
Stewart et al.; Hypoxic Respiratory Failure: Diagnosis and Treatment, 36th Annual Pacific Northwest Regional Respiratory Care Conference and Scientific Assembly; Apr. 26, 2009; pp. 1-71.
Stork et al., "Inhaled Nitric Oxide in Full-Term and Nearly Full-Term Infants with Hypoxic Respiratory Failure," Feb. 27, 1997, 336(9): 597-604.
Strauss et al., "Pediatric Cardiomyopathy—A Long Way to Go," The New England Journal of Medicine, vol. 348, No. 17, pp. 1703-1705 (2003).
Subhedar et al., "Changes in oxygenation and pulmonary haemodynamics in preterm infants treated with inhaled nitric oxide," Archives of Disease in Childhood, 1997, 77:F191-F197.
Subhedar et al., "Is nitric oxide effective in preterm infants?" Arch. Dis. Child Fetal Neonatal Ed., 2007, 92: 337-341.
Subhedar et al., "Open randomised controlled trial of inhaled nitric oxide and early dexamethasone in high risk preterm infants," Archives of Disease in Childhood, 1997, 77: F185-F190.
Sugimoto et al., "Echocardiographic estimation of pulmonary capillary wedge pressure using the combination of diastolic annular and mitral inflow velocities," J. Echocardiogr., 2013, 11: 1-8.
Sussman et al., "Successful Liver Transplantation Following Medical Management of Portopulmonary Hypertension," A Single-Center Series: American Journal of Transplantation, 2006, 6: 2177-2182.
Ter Horst et al., "Inhaled nitric oxide attenuates pulmonary inflammation and fibrin deposition and prolongs survival in neonatal hyperoxic lung injury," Am. J. Physiol. Lung Cell Mol. Physiol., 2007, 293: L35-L44.
The American Illustrated Medical Dictionary (Dorland, 7th ed., p. 113) (1914).
The Effects of Nitric Oxide for Inhalation on the Development of Chronic Lung Disease in Pre-Term Infants, from ClinicalTrials.gov archive, NCT00551642, Oct. 30, 2007, 3 pages.
The Encarta Webster's Dictionary of the English Language (2004) is the second edition of the Encarta World Dictionary, published 1999, «http://encarta.msn.com/encnel/features/dictionary/dictionaryhome.aspx»; used to look up the definitions of "precaution" and "exclusion".
The Neonatal Inhaled Nitric Oxide Study Group, "Inhaled Nitric Oxide in Full-Term and Nearly Full-Term Infants with Hypoxic Respiratory Failure." N. Engl. J_ Med., vol. 336, No. 9, pp. 597-605 (1997).
The Neonatal Inhaled Nitric Oxide Study Group, The New England Journal of Medicine, vol. 336(9), pp. 597-604 (1997).
The NIH, Critical Care Therapy and Respiratory Care Section, Nitric Oxide Therapy, 13 pages (2000).
Torys LLP, Letter to Canadian Commissioner of Patents relating to CA 2,671,029; Aug. 9, 2013.
Toshmiwal, et al., "Study of Comparative Effects of Oral Clondine vs. Oral Diazepam Pre-medication on the Extent and Duration of Sensory Blockade in Patients Undergoing Vaginal Hysterectomy Under Spinal Anesthesia", Internet Journal of Anesthesiology (2009) http://www.britannica.com/bps/additionalcontenl/18/41575551/Study-of- Comparative-Effects-Oral-Clonidine-vs-Oral-Diazepam-Pre-Medication-on-the-Extent-and-Duration-of-Sensory-Blockade-in-Patients-Undergoing-Vaginal-Hysterectomy-Under-Spinal-Anaesthesia>>.

(56) References Cited

OTHER PUBLICATIONS

Towbin et al., "Incidence, Causes, and Outcomes of Dilated Cardiomyopathy in Children," JAMA, vol. 296, No. 15, pp. 1867-1876 (2006).
Japanese Office Action dated Feb. 15. 2011 for Japanese Patent Application No. 2009-157623. a counterpart foreign application for U.S. Appl. No. 12/494,598.
Troncy et al. "Inhaled nitric oxide: clinical applications, indications, and toxicology." Can. J_ Anaesth. vol. 44 (9). pp. 972-988 (1997).
Truog, "Inhaled Nitric Oxide: A Tenth Anniversary Observation," Pediatrics, 1998, 101: 696.
Turanlahti et al., "Nitric oxide, oxygen, and prostacyclin in children with pulmonary hypertension," Heart, 1998, 79: 169-174.
Advisory Action in U.S. Appl. No. 12/820,866, dated Feb. 23, 2011 (2 pages).
Advisory Action in U.S. Appl. No. 12/820,866, dated Mar. 25, 2011 (3 pages).
Advisory Action in U.S. Appl. No. 12/820,980, dated Nov. 29, 2010 (3 pages).
Examiner's Answer in U.S. Appl. No. 12/820,866, dated Nov. 2, 2011 (27 pages).
Interview Summary in U.S. Appl. No. 12/821,020, dated Jan. 25, 2012 (4 pages).
Notice of Abandonment in U.S. Appl. No. 12/494,598, dated Sep. 10, 2010 (2 pages).
Notice of Abandonment in U.S. Appl. No. 12/820,866, dated Dec. 20, 2012 (2 pages).
Notice of Abandonment in U.S. Appl. No. 12/820,980, dated Apr. 11, 2012 (2 pages).
Office Action in U.S. Serial No. 12/494,598, dated Aug. 13, 2010 (26 pages).
Office Action in U.S. Appl. No. 12/820,866, filed Aug. 24, 2011 (23 pages).
Office Action in U.S. Appl. No. 12/820,866, dated Jun. 8, 2011 (32 pages).
Office Action in U.S. Appl. No. 12/820,866, dated Nov. 2, 2010 (25 pages).
Office Action in U.S. Appl. No. 12/820,866, dated Sep. 23, 2010 (26 pages).
Office Action in U.S. Appl. No. 12/820,980, dated Aug. 17, 2010 (33 pages).
Office Action in U.S. Appl. No. 12/820,980, dated Jun. 10, 2011 (29 pages).
Office Action in U.S. Appl. No. 12/820,980, dated Oct. 28, 2010 (23 pages).
Office Action in U.S. Appl. No. 12/820,980, dated Sep. 9, 2011 (25 pages).
Office Action in U.S. Appl. No. 12/821,020, dated Aug. 13, 2010 (24 pages).
Office Action in U.S. Appl. No. 12/821,020, dated Jan. 31, 2012 (23 pages).
Office Action in U.S. Appl. No. 12/821,020, dated Jun. 15, 2012 (56 pages).
Office Action in U.S. Appl. No. 12/821,020, dated Jun. 27, 2011 (28 pages).
Office Action in U.S. Appl. No. 12/821,041, dated Aug. 17, 2010 (32 pages).
Office Action in U.S. Appl. No. 12/821,041, dated Feb. 10, 2012 (36 pages).
Office Action in U.S. Appl. No. 12/821,041, dated Jun. 19, 2012 (61 pages).
Office Action in U.S. Appl. No. 12/821,041, dated Jun. 27, 2011 (35 pages).
Supplemental Office Action in U.S. Appl. No. 12/820,980, dated Nov. 2, 2010 (4 pages).
USPTO Notice of Abandonment in U.S. Appl. No. 14/451,057, dated Dec. 16, 2015, 2 pages.
USPTO Notice of Abandonment in U.S. Appl. No. 14/454,373, dated Dec. 1, 2015, 2 pages.
USPTO Notice of Abandonment in U.S. Appl. No. 14/482,704, dated Mar. 14, 2016, 2 pages.
Interview Summary in U.S. Appl. No. 12/821,020, dated Apr. 17, 2012 (4 pages).
UCI General Clinical Research Center. Federal Regulations 21 CFR Part 312. «http://www.gcrc.uci.edu/rsa/aer. cfm». retrieved Sep. 13, 2010. 2 pages.
University of Alabama. NCT00732537 at Clinicaltrials.gov (2008).
UTMB Respiratory Care Services. "Delivery of Inhaled Nitric Oxide Therapy through an Adult or Pediatric Nasal Cannula." 4 pages. (2003).
Van Dalen. "Treatment for Asymptomatic Anthracycline-induced Cardiac Dysfunction in Childhood Cancer Survivors: The Need for Evidence." Journal of Clinical Oncology. vol. 21. No 17. pp. 3375-3379 (2003).
Van Meurs et al., "Inhaled Nitric Oxide for Premature Infants with Severe Respiratory Failure," N. Engl. J. Med., 2005: 353: 13-22.
Vonbank et al., "Controlled prospective randomised trial on the effects on pulmonary haemodynamics of the ambulatory long term use of nitric oxide and oxygen in patients with severe COPD," Thorax, 2003, 58: 289-293.
Waldmann et al., Oxford Desk Reference Critical Care, Oxford University Press, 2008, 1-4.
Ware, "Inhaled Nitric Oxide in Infants and Children," Crit. Care Nurs. Clin. North Am., Mar. 2002, 14(1): 1-6.
Watson et al., "Clinical and Economic Effects of iNO in Premature Newborns With Respiratory Failure at 1 Year." Pediatrics. vol. 124. pp. 1333-1343 (2009).
Webster's II New College Dictionary, Houghton Mifflin Company, @1995, p. 194.
Weinberger et al., "Nitric Oxide in the lung: therapeutic and cellular mechanisms of action". Pharmacology & Therapeutics. vol. 84. pp. 401-411 (1999).
Weinberger et al., "The Toxicology of Inhaled Nitric Oxide." Toxicological Sciences. vol. 59. pp. 5-16 (2001).
Weinberger et al., Pulmonary Hypertension, Chapter 14 of Principles of Pulmonary Medicine, Elsevier Saunders, 2014, pp. 189-200.
Wessel et al., "Improved Oxygenation in a Randomized Trial of Inhaled Nitric Oxide for Persistent Pulmonary Hypertension of the Newborn." Pediatrics. vol. 100. No. 5. p. E7 (1997).
Wessel et al., "Managing low cardiac output syndrome after congenital heart surgery," Crit. Care Med., vol. 29(10) pp. S220-S230 (2001).
Wessel, "Commentary: Simple Gases and Complex Single Ventricles," J. of Thoracic and Cardiovascular Surgery, Sep. 1996, 112:3 655-57.
Wessel, "Current and future strategies in the treatment of childhood pulmonary hypertension," Progress in Pediatric Cardiology, 2001, 12: 289-318.
Wheeler et al., "The Central Nervous System in Pediatric Critical Illness and Injury," Pediatric Critical Care Medicine, Springer, p. 278 (2007).
Widlitz et al., "Pulmonary arterial hypertension in children," European Respiratory Journal, Jan. 2003, 1-47.
Wilkinson et al., "Epidemiological and outcomes research in children with pediatric cardiomyopathy; discussions from the international workshop on primary and idiopathic cardiomyopathies in children," Progress in Pediatric Cardiology, Apr. 2008, 25(1): 23. www.fda.gov/downloads/Drugs/GuidanceComplianceRegulatoryInformation/Guidance/ucm073087. pdf, Mar. 1995.
Yamashita et al., "Resistance to Endotoxin Shock in Transgenic Mice Overexpressing Endothelial Nitric Oxide Synthase," Circulation, 2000, 101: 931-937.
Yoshida, "Well-illustrated Diagnostics and Treatment of Heart Failure,", Circulation, vol. 2, No. 4, pp. 23-28 (2007).
Ziegler et al., "Effects of Dipyridamole and Inhaled Nitric Oxide in Pediatric Patients with Pulmonary Hypertension," Am. J. Respir. Crit. Care Med., 1998, 158: 1388-1395.
Zile et al., "New Concepts in Diastolic Dysfunction and Diastolic Heart Failure: Part I—Diagnosis, Prognosis, and Measurements of Diastolic Function," Circulation, Mar. 19, 2002, 105: 1387-1392.

(56) References Cited

OTHER PUBLICATIONS

Zile et al., "New Concepts in Diastolic Dysfunction and Diastolic Heart Failure: Part II—Causal Mechanisms and Treatment," Circulation, 2002, 105: 1503-1508.
U.S. Appl. No. 12/494,598, Baldassarre et al., filed Jun. 30, 2009 (abandoned).
U.S. Appl. No. 12/820,866, Baldassarre et al., filed Jun. 22, 2010 (abandoned).
U.S. Appl. No. 12/820,980, Baldassarre et al., filed Jun. 22, 2010 (abandoned).
U.S. Appl. No. 13/683,444, Baldassarre, filed Nov. 21, 2012.
U.S. Appl. No. 14/451,057, Baldassarre, filed Aug. 4, 2014 (abandoned).
U.S. Appl. No. 14/454,373, Baldassarre, filed Aug. 7, 2014 (abandoned).
U.S. Appl. No. 14/482,704, Baldassarre, filed Sep. 10, 2014 (abandoned).
Benza et al., "Pulmonary hypertension related to left heart disease: insight from a wireless implantable hemodynamic monitor," J Heart Lung Transplant, Mar. 2015, 34(3): 329-337.
Abman, "Inhaled nitric oxide therapy of severe neonatal pulmonary hypertension," Acta Anaesthesiologica Scandinavica, Jun. 1995, 39: 65-68.
Kinsella et al., "Randomized, multicenter trial of inhaled nitric oxide and high-frequency oscillatory ventilation in severe, persistent pulmonary hypertension of the newborn," J Pediatics, Jul. 1997, 131(1): 55-62.
Kinsella and Abman, "Controversies in the use of Inhaled Nitric Oxide Therapy in the Newborn," Clin Perinatol, Mar. 1998, 25(1): 203-217.
*INO Therapeutics* v. *Praxair*, case 2018-1019 (Fed. Cir. Aug. 27, 2019), 34 pages.
*Praxair* v. *Mallinckrodt*, case 2016-2616, 2016-2656 (Fed. Cir. May 16, 2018), 30 pages.
Steinhorn, "Neonatal pulmonary hypertension," Pediatr Crit Care Med, Mar. 2010, 11 (2 (Suppl.)), S79-S84.
Rihal et al., "Systolic and diastolic dysfunction in patients with clinical diagnosis of dilated cardiomyopathy. Relation to symptoms and prognosis," Circulation, Dec. 1, 1994, 90(6):2772-2779.
Satpathy et al., "Diagnosis and Management of Diastolic Dysfunction and Heart Failure," Am Fam Physician, Mar. 1, 2006, 73(5):841-846.
CA Commissioner's Decision in Canadian Appln. No. 2671029, dated Mar. 19, 2021, 27 pages.

* cited by examiner

METHODS OF ADMINISTERING INHALED NITRIC OXIDE GAS

CROSS REFERENCE TO RELATED APPLICATIONS

This application is a divisional of U.S. application Ser. No. 13/683,444, filed Nov. 21, 2012, which is a divisional of U.S. application Ser. No. 12/820,866, filed Jun. 22, 2010, and now abandoned, which is a continuation of U.S. Ser. No. 12/494,598, filed Jun. 30, 2009, and now abandoned. U.S. application Ser. No. 13/683,444 is also a divisional of U.S. Ser. No. 13/651,660 (now U.S. Pat. No. 8,431,163), filed Oct. 15, 2012, which is a continuation of U.S. application Ser. No. 12/821,041 (now U.S. Pat. No. 8,293,284), filed Jun. 22, 2010, which is a continuation of U.S. application Ser. No. 12/494,598, filed Jun. 30, 2009, and now abandoned. The contents of all of the above applications are hereby incorporated by reference.

BACKGROUND OF THE INVENTION

INOmax®, (nitric oxide) for inhalation is an approved drug product for the treatment of term and near-term (>34 weeks gestation) neonates having hypoxic respiratory failure associated with clinical or echocardiographic evidence of pulmonary hypertension.

The use of inhaled NO (iNO) has been studied and reported in the literature. (Kieler-Jensen M et al., 1994, Inhaled Nitric Oxide in the Evaluation of Heart Transplant Candidates with Elevated Pulmonary Vascular Resistance, *J Heart Lung Transplantation* 13:366-375; Pearl R G et al., 1983, Acute Hemodynamic Effects of Nitroglycerin in Pulmonary Hypertension, *American College of Physicians* 99:9-13; Ajami G H et al., 2007, Comparison of the Effectiveness of Oral Sildenafil Versus Oxygen Administration as a Test for Feasibility of Operation for Patients with Secondary Pulmonary Arterial Hypertension, *Pediatr Cardiol;* Schulze-Neick I et al., 2003, Intravenous Sildenafil Is a Potent Pulmonary Vasodilator in Children With Congenital Heart Disease, *Circulation* 108(Suppl II):II-167-II-173; Lepore J J et al., 2002, Effect of Sildenafil on the Acute Pulmonary Vasodilator Response to Inhaled Nitric Oxide in Adults with Primary Pulmonary Hypertension, *The American Journal of Cardiology* 90:677-680; and Ziegler J W et al., 1998, Effects of Dipyridamole and Inhaled Nitric Oxide in Pediatric Patients with Pulmonary Hypertension, *American Journal of Respiratory and Critical Care Medicine* 158:1388-95).

SUMMARY OF THE INVENTION

One aspect of the invention relates to a pre-screening methodology or protocol having exclusionary criteria to be evaluated by a medical provider prior to treatment of a patient with iNO. One objective of the invention is to evaluate and possibly exclude from treatment patients eligible for treatment with iNO, who have pre-existing left ventricular dysfunction (LVD). Patients who have pre-existing LVD may experience, and are at risk of, an increased rate of adverse events or serious adverse events (e.g., pulmonary edema) when treated with iNO. Such patients may be characterized as having a pulmonary capillary wedge pressure (PCWP) greater than 20 mm Hg, and should be evaluated on a case-by-case basis with respect to the benefit versus risk of using iNO as a treatment option.

Accordingly, one aspect of the invention includes a method of reducing the risk or preventing the occurrence, in a human patient, of an adverse event (AE) or a serious adverse event (SAE) associated with a medical treatment comprising inhalation of nitric oxide, said method comprising the steps or acts of (a) providing pharmaceutically acceptable nitric oxide gas to a medical provider; and, (b) informing the medical provider that excluding human patients who have pre-existing left ventricular dysfunction from said treatment reduces the risk or prevents the occurrence of the adverse event or the serious adverse event associated with said medical treatment.

Further provided herein is a method of reducing the risk or preventing the occurrence, in a human patient, of an adverse event or a serious adverse event associated with a medical treatment comprising inhalation of nitric oxide, said method comprising the steps or acts of (a) providing pharmaceutically acceptable nitric oxide gas to a medical provider; and, (b) informing the medical provider that human patients having pre-existing left ventricular dysfunction experience an increased risk of serious adverse events associated with said medical treatment.

Another aspect of the invention is a method of reducing one or more of an AE or a SAE in an intended patient population in need of being treated with iNO comprising the steps or acts of (a) identifying a patient eligible for iNO treatment; (b) evaluating and screening the patient to identify if the patient has pre-existing LVD, and (c) excluding from iNO treatment a patient identified as having pre-existing LVD.

Another aspect of the invention is a method of reducing the risk or preventing the occurrence, in a patient, of one or more of an AE or a SAE associated with a medical treatment comprising iNO, the method comprising the steps or acts of (a) identifying a patient in need of receiving iNO treatment; (b) evaluating and screening the patient to identify if the patient has pre-existing LVD; and (c) administering iNO if the patient does not have pre-existing LVD, thereby reducing the risk or preventing the occurrence of the AE or the SAE associated with the iNO treatment. Alternatively, step (c) may comprise further evaluating the risk versus benefit of utilizing iNO in a patient where the patients has clinically significant LVD before administering iNO to the patient.

In an exemplary embodiment of the method, the method further comprises informing the medical provider that there is a risk associated with using inhaled nitric oxide in human patients who have preexisting or clinically significant left ventricular dysfunction and that such risk should be evaluated on a case by case basis.

In another exemplary embodiment of the method, the method further comprises informing the medical provider that there is a risk associated with using inhaled nitric oxide in human patients who have left ventricular dysfunction.

In an exemplary embodiment of the methods described herein, a patient having pre-existing LVD is characterized as having PCWP greater than 20 mm Hg.

In an exemplary embodiment of the method, the patients having pre-existing LVD demonstrate a PCWP≥20 mm Hg.

In another exemplary embodiment of the method, the iNO treatment further comprises inhalation of oxygen ($O_2$) or concurrent ventilation.

In another exemplary embodiment of the method, the patients having pre-existing LVD have one or more of diastolic dysfunction, hypertensive cardiomyopathy, systolic dysfunction, ischemic cardiomyopathy, viral cardiomyopathy, idiopathic cardiomyopathy, autoimmune disease related cardiomyopathy, drug-related cardiomyopathy, toxin-related cardiomyopathy, structural heart disease, valvular heart disease, congenital heart disease, or associations thereof.

In another exemplary embodiment of the method, the patient population comprises children.

In another exemplary embodiment of the method, the patient population comprises adults.

In another exemplary embodiment of the method, the patients who have pre-existing LVD are at risk of experiencing an increased rate of one or more AEs or SAEs selected from pulmonary edema, hypotension, cardiac arrest, electrocardiogram changes, hypoxemia, hypoxia, bradycardia, or associations thereof.

In another exemplary embodiment of the method, the intended patient population in need of being treated with inhalation of nitric oxide has one or more of idiopathic pulmonary arterial hypertension characterized by a mean pulmonary artery pressure (PAPm)>25 mm Hg at rest, PCWP≤15 mm Hg, and a pulmonary vascular resistance index (PVRI)>3 u·m$^2$; congenital heart disease with pulmonary hypertension repaired and unrepaired characterized by PAPm>25 mm Hg at rest and PVRI>3 u·m$^2$; cardiomyopathy characterized by PAPm>25 mm Hg at rest and PVRI>3 u·m$^2$; or the patient is scheduled to undergo right heart catheterization to assess pulmonary vasoreactivity by acute pulmonary vasodilatation testing.

In another exemplary embodiment of any of the above methods, the method further comprises reducing left ventricular afterload to minimize or reduce the risk of the occurrence of an adverse event or serious adverse event being pulmonary edema in the patient. The left ventricular afterload may be minimized or reduced by administering a pharmaceutical dosage form comprising nitroglycerin or calcium channel blocker to the patient. The left ventricular afterload may also be minimized or reduced using an intra-aortic balloon pump.

DETAILED DESCRIPTION OF THE EXEMPLARY EMBODIMENTS

INOmax® (nitric oxide) for inhalation was approved for sale in the United States by the U.S. Food and Drug Administration ("FDA") in 1999. Nitric oxide, the active substance in INOmax®, is a selective pulmonary vasodilator that increases the partial pressure of arterial oxygen (PaO$_2$) by dilating pulmonary vessels in better ventilated areas of the lung, redistributing pulmonary blood flow away from the lung regions with low ventilation/perfusion (V/Q) ratios toward regions with normal ratios. INOmax® significantly improves oxygenation, reduces the need for extracorporeal oxygenation, and is indicated to be used in conjunction with ventilatory support and other appropriate agents. The FDA-approved prescribing information for INOmax® in effect at the Jun. 30, 2009, priority date is incorporated herein by reference in its entirety. The DOSAGE section of the prescribing information for INOmax® states that the recommended dose of INOmax® is 20 ppm, and that treatment should be maintained up to 14 days or until the underlying oxygen desaturation has resolved and the neonate is ready to be weaned from INOmax® therapy. The CONTRAINDICATIONS section of the prescribing information for INOmax® states that INOmax® should not be used in the treatment of neonates known to be dependent on right-to-left shunting of blood.

INOmax® is a gaseous blend of NO and nitrogen (0.08% and 99.92% respectively for 800 ppm; and 0.01% and 99.99% respectively for 100 ppm) and is supplied in aluminium cylinders as a compressed gas under high pressure. In general, INOmax® is administered to a patient in conjunction with ventilatory support and O$_2$. Delivery devices suitable for the safe and effective delivery of gaseous NO for inhalation include the INOvent®, INOmax DS®, INOpulse®, INOblender®, or other suitable drug delivery and regulation devices or components incorporated therein, or other related processes, which are described in various patent documents including U.S. Pat. Nos. 5,558,083; 5,732,693; 5,752,504; 5,732,694; 6,089,229; 6,109,260; 6,125,846; 6,164,276; 6,581,592; 5,918,596; 5,839,433; 7,114,510; 5,417,950; 5,670,125; 5,670,127; 5,692,495; 5,514,204; 7,523,752; 5,699,790; 5,885,621; U.S. patent application Ser. No. 11/355,670 (US 2007/0190184); Ser. No. 10/520,270 (US 2006/0093681); Ser. No. 11/401,722 (US 2007/0202083); Ser. No. 10/053,535 (US 2002/0155166); Ser. No. 10/367,277 (US 2003/0219496); Ser. No. 10/439,632 (US 2004/0052866); Ser. No. 10/371,666 (US 2003/0219497); Ser. No. 10/413,817 (US 2004/0005367); Ser. No. 12/050,826 (US 2008/0167609); and PCT/US2009/045266, all of which are incorporated herein by reference in their entirety.

Such devices deliver INOmax® into the inspiratory limb of the patient breathing circuit in a way that provides a constant concentration of NO to the patient throughout the inspired breath. Importantly, suitable delivery devices provide continuous integrated monitoring of inspired O$_2$, NO$_2$ and NO, a comprehensive alarm system, a suitable power source for uninterrupted NO delivery, and a backup NO delivery capability.

As used herein, the term "children" (and variations thereof) includes those being around 4 weeks to 18 years of age.

As used herein, the term "adult" (and variations thereof) includes those being over 18 years of age.

As used herein, the terms "adverse event" and "AE" (and variations thereof) mean any untoward occurrence in a subject or clinical investigation subject administered a pharmaceutical product (such as nitric oxide) and which does not necessarily have a causal relationship with such treatment. An adverse event can therefore be any unfavorable and unintended sign (including an abnormal laboratory finding), symptom, or disease temporarily associated with the use of a medicinal/investigational product, whether or not related to the investigational product. A relationship to the investigational product is not necessarily proven or implied. However, abnormal values are not reported as adverse events unless considered clinically significant by the investigator.

As used herein, the terms "adverse drug reaction" and "ADR" (and variations thereof) mean any noxious and unintended response to a medicinal product related to any dose.

As used herein, the terms "serious adverse event" and "SAE" (or "serious adverse drug reaction" and "serious ADR") (and variations thereof) mean a significant hazard or side effect, regardless of the investigator's opinion on the relationship to the investigational product. A serious adverse event or reaction is any untoward medical occurrence that at any dose: results in death; is life-threatening (which refers to an event/reaction where the patient was at risk of death at the time of the event/reaction, however this does not refer to an event/reaction that hypothetically may have caused death if it were more severe); requires inpatient hospitalization or results in prolongation of existing hospitalization; results in persistent or significant disability/incapacity; is a congenital anomaly/birth defect; or is a medically important event or reaction. Medical and scientific judgment is exercised in deciding whether reporting is appropriate in other situations, such as important medical events that may not be immediately life threatening or result in death or hospitalization but may jeopardize the subject or may require medical or surgical intervention to prevent one of the other outcomes listed above—these are also considered serious. Examples of such medical events include cancer, allergic bronchospasm requiring intensive treatment in an emergency room or at home, blood dyscrasias or convulsions that do not result in hospitalizations, or the development of drug dependency or drug abuse. Serious clinical laboratory abnormalities directly associated with relevant clinical signs or symptoms are also reported.

Left Ventricular Dysfunction. Patients having pre-existing LVD may be described in general as those with elevated pulmonary capillary wedge pressure, including those with diastolic dysfunction (including hypertensive cardiomyopathy), those with systolic dysfunction, including those with cardiomyopathies (including ischemic or viral cardiomyopathy, or idiopathic cardiomyopathy, or autoimmune disease related cardiomyopathy, and side effects due to drug related or toxic-related cardiomyopathy), or structural heart disease, valvular heart disease, congenital heart disease, idiopathic pulmonary arterial hypertension, pulmonary hypertension and cardiomyopathy, or associations thereof. Identifying patients with pre-existing LVD is known to those skilled in the medicinal arts, and such techniques for example may include assessment of clinical signs and symptoms of heart failure, or echocardiography diagnostic screening.

Pulmonary Capillary Wedge Pressure. Pulmonary capillary wedge pressure, or "PCWP", provides an estimate of left atrial pressure. Identifying patients with pre-existing PCWP is known to those skilled in the medicinal arts, and such techniques for example may include measuring by inserting a balloon-tipped, multi-lumen catheter (also known as a Swan-Ganz catheter). Measurement of PCWP may be used as a means to diagnose the severity of LVD (sometimes also referred to as left ventricular failure). PCWP is also a desired measure when evaluating pulmonary hypertension. Pulmonary hypertension is often caused by an increase in pulmonary vascular resistance (PVR), but may also arise from increases in pulmonary venous pressure and pulmonary blood volume secondary to left ventricular failure or mitral or aortic valve disease.

In cardiac physiology, the term "afterload" is used to mean the tension produced by a chamber of the heart in order to contract. If the chamber is not mentioned, it is usually assumed to be the left ventricle. However, the strict definition of the term relates to the properties of a single cardiac myocyte. It is therefore of direct relevance only in the laboratory; in the clinic, the term "end-systolic pressure" is usually more appropriate, although not equivalent.

The term "left ventricular afterload" (and variations thereof) refers to the pressure that the chamber of the heart has to generate in order to eject blood out of the chamber. Thus, it is a consequence of the aortic pressure, since the pressure in the ventricle must be greater than the systemic pressure in order to open the aortic valve. Everything else held equal, as afterload increases, cardiac output decreases. Disease processes that increase the left ventricular afterload include increased blood pressure and aortic valve disease. Hypertension (increased blood pressure) increases the left ventricular afterload because the left ventricle has to work harder to eject blood into the aorta. This is because the aortic valve won't open until the pressure generated in the left ventricle is higher than the elevated blood pressure. Aortic stenosis increases the afterload because the left ventricle has to overcome the pressure gradient caused by the stenotic aortic valve in addition to the blood pressure in order to eject blood into the aorta. For instance, if the blood pressure is 120/80, and the aortic valve stenosis creates a trans-valvular gradient of 30 mmHg, the left ventricle has to generate a pressure of 110 mmHg in order to open the aortic valve and eject blood into the aorta. Aortic insufficiency increases afterload because a percentage of the blood that is ejected forward regurgitates back through the diseased aortic valve. This leads to elevated systolic blood pressure. The diastolic blood pressure would fall, due to regurgitation. This would result in an increased pulse pressure. Mitral regurgitation decreases the afterload. During ventricular systole, the blood can regurgitate through the diseased mitral valve as well as be ejected through the aortic valve. This means that the left ventricle has to work less to eject blood, causing a decreased afterload. Afterload is largely dependent upon aortic pressure.

An intra-aortic balloon pump (IABP) is a mechanical device that is used to decrease myocardial oxygen demand while at the same time increasing cardiac output. By increasing cardiac output it also increases coronary blood flow and therefore myocardial oxygen delivery. It consists of a cylindrical balloon that sits in the aorta and counterpulsates. That is, it actively deflates in systole, increasing forward blood flow by reducing afterload, and actively inflates in diastole increasing blood flow to the coronary arteries. These actions have the combined result of decreasing myocardial oxygen demand and increasing myocardial oxygen supply. The balloon is inflated during diastole by a computer controlled mechanism, usually linked to either an ECG or a pressure transducer at the distal tip of the catheter; some IABPs, such as the Datascope System 98XT, allow for asynchronous counterpulsation at a set rate, though this setting is rarely used. The computer controls the flow of helium from a cylinder into and out of the balloon. Helium is used because its low viscosity allows it to travel quickly through the long connecting tubes, and it has a lower risk of causing a harmful embolism should the balloon rupture while in use. Intraaortic balloon counterpulsation is used in situations when the heart's own cardiac output is insufficient to meet the oxygenation demands of the body. These situations could include cardiogenic shock, severe septic shock, post cardiac surgery and numerous other situations.

Patients eligible for treatment with iNO. In general, patients approved for treatment of iNO are term and near-term (>34 weeks gestation) neonates having hypoxic respiratory failure associated with clinical or echocardiographic evidence of pulmonary hypertension, a condition also known as persistent pulmonary hypertension of the newborn (PPHN). Due to the selective, non-systemic nature of iNO to reduce pulmonary hypertension, physicians skilled in the art further employ INOmax® to treat or prevent pulmonary hypertension and improve blood $O_2$ levels in a variety of other clinical settings, including in both pediatric and adult patients suffering from acute respiratory distress syndrome (ARDS), pediatric and adult patients undergoing cardiac or transplant surgeries, pediatric and adult patients for testing to diagnose reversible pulmonary hypertension, and in pediatric patients with congenital diaphragmatic hernia. In most, if not all, of these applications, INOmax® acts by preventing or treating reversible pulmonary vasoconstriction, reducing pulmonary arterial pressure and improving pulmonary gas exchange.

A small proportion of INOmax® sales stem from its use by clinicians in a premature infant population. In these patients, INOmax® is generally utilized by physicians as a rescue therapy primarily to vasodilate the lungs and improve pulmonary gas exchange. Some physicians speculate that INOmax® therapy may promote lung development and/or reduce or prevent the future development of lung disease in a subset of these patients. Although the precise mechanism(s) responsible for the benefits of INOmax® therapy in these patients is not completely understood, it appears that the benefits achieved in at least a majority of these patients are due to the ability of INOmax® to treat or prevent reversible pulmonary vasoconstriction.

In clinical practice, the use of INOmax® has reduced or eliminated the use of high risk systemic vasodilators for the treatment of PPHN. INOmax®, in contrast to systemic vasodilators, specifically dilates the pulmonary vasculature without dilating systemic blood vessels. Further, iNO preferentially vasodilates vessels of aveoli that are aerated, thus improving V/Q matching. In contrast, systemic vasodilators may increase blood flow to atelectatic (deflated or collapsed) alveoli, thereby increasing V/Q mismatch and worsening arterial oxygenation. (See Rubin L J, Kerr K M, Pulmonary Hypertension, in *Critical Care Medicine: Principles of Diagnosis and Management in the Adult, 2d Ed.*, Parillo J E, Dellinger R P (eds.), Mosby, Inc. 2001, pp. 900-09 at 906; Kinsella J P, Abman S H, The Role of Inhaled Nitric Oxide in Persistent Pulmonary Hypertension of the Newborn, in *Acute Respiratory Care of the Neonate: A Self-Study Course, 2d Ed.*, Askin D F (ed.), NICU Ink Book Publishers, 1997, pp. 369-378 at 372-73).

INOmax® also possesses highly desirable pharmacokinetic properties as a lung-specific vasodilator when compared to other ostensibly "pulmonary-specific vasodilators." For example, the short half-life of INOmax® allows INOmax® to exhibit rapid "on" and "off" responses relative to INOmax® dosing, in contrast to non-gaseous alternatives. In this way, INOmax® can provide physicians with a useful therapeutic tool to easily control the magnitude and duration of the pulmonary vasodilatation desired. Also, the nearly instantaneous inactivation of INOmax® in the blood significantly reduces or prevents vasodilatation of non-pulmonary vessels.

The pivotal trials leading to the approval of INOmax® were the CINRGI and NINOS study.

CINRGI study. (See Davidson et al., March 1998, Inhaled Nitric Oxide for the Early Treatment of Persistent Pulmonary Hypertension of the term Newborn; A Randomized, Double-Masked, Placebo-Controlled, Dose-Response, Multicenter Study; *PEDIATRICS* Vol. 101, No. 3, p. 325).

This study was a double-blind, randomized, placebo-controlled, multicenter trial of 186 term and near-term neonates with pulmonary hypertension and hypoxic respiratory failure. The primary objective of the study was to determine whether INOmax® would reduce the receipt of extracorporeal membrane oxygenation (ECMO) in these patients. Hypoxic respiratory failure was caused by meconium aspiration syndrome (MAS) (35%), idiopathic persistent pulmonary hypertension of the newborn (PPHN) (30%), pneumonia/sepsis (24%), or respiratory distress syndrome (RDS) (8%). Patients with a mean $PaO_2$ of 54 mm Hg and a mean oxygenation index (OI) of 44 cm $H_2O$/mm Hg were randomly assigned to receive either 20 ppm INOmax® (n=97) or nitrogen gas (placebo; n=89) in addition to their ventilatory support. Patients that exhibited a $PaO_2$>60 mm Hg and a pH<7.55 were weaned to 5 ppm INOmax® or placebo. The primary results from the CINRGI study are presented in Table 1. ECMO was the primary endpoint of the study.

TABLE 1

Summary of Clinical Results from CINRGI Study

|  | Placebo | INOmax ® | P value |
|---|---|---|---|
| Death or ECMO | 51/89 (57%) | 30/97 (31%) | <0.001 |
| Death | 5/89 (6%) | 3/97 (3%) | 0.48 |

Significantly fewer neonates in the ECMO group required ECMO, and INOmax® significantly improved oxygenation, as measured by $PaO_2$, OI, and alveolar-arterial gradient.

NINOS study. (See Inhaled Nitric Oxide in Full-Term and Nearly Full-Term Infants with Hypoxic Respiratory Failure; NEJM, Vol. 336, No. 9, 597).

The Neonatal Inhaled Nitric Oxide Study (NINOS) group conducted a double-blind, randomized, placebo-controlled, multicenter trial in 235 neonates with hypoxic respiratory failure. The objective of the study was to determine whether iNO would reduce the occurrence of death and/or initiation of ECMO in a prospectively defined cohort of term or near-term neonates with hypoxic respiratory failure unresponsive to conventional therapy. Hypoxic respiratory failure was caused by meconium aspiration syndrome (MAS; 49%), pneumonia/sepsis (21%), idiopathic primary pulmonary hypertension of the newborn (PPHN; 17%), or respiratory distress syndrome (RDS; 11%). Infants≤14 days of age (mean, 1.7 days) with a mean $PaO_2$ of 46 mm Hg and a mean oxygenation index (OI) of 43 cm $H_2O$/mmHg were initially randomized to receive 100% $O_2$ with (n=114) or without (n=121) 20 ppm NO for up to 14 days. Response to study drug was defined as a change from baseline in $PaO_2$ 30 minutes after starting treatment (full response=>20 mmHg, partial=10-20 mm Hg, no response=<10 mm Hg). Neonates with a less than full response were evaluated for a response to 80 ppm NO or control gas. The primary results from the NINOS study are presented in Table 2.

TABLE 2

Summary of Clinical Results from NINOS Study

|  | Control (n = 121) | NO (n = 114) | P value |
|---|---|---|---|
| Death or ECMO*, † | 77 (64%) | 52 (46%) | 0.006 |
| Death | 20 (17%) | 16 (14%) | 0.60 |
| ECMO | 66 (55%) | 44 (39%) | 0.014 |

*Extracorporeal membrane oxygenation
† Death or need for ECMO was the study's primary end point Adverse Events from CINRGI & NINOS. Controlled studies have included 325 patients on INOmax® doses of 5 to 80 ppm and 251 patients on placebo. Total mortality in the pooled trials was 11% on placebo and 9% on INOmax®, a result adequate to exclude INOmax® mortality being more than 40% worse than placebo.

In both the NINOS and CINRGI studies, the duration of hospitalization was similar in INOmax® and placebo-treated groups.

From all controlled studies, at least 6 months of follow-up is available for 278 patients who received INOmax® and 212 patients who received placebo. Among these patients, there was no evidence of an AE of treatment on the need for re-hospitalization, special medical services, pulmonary disease, or neurological sequelae.

In the NINOS study, treatment groups were similar with respect to the incidence and severity of intracranial hemorrhage, Grade IV hemorrhage, per ventricular leukomalacia, cerebral infarction, seizures requiring anticonvulsant therapy, pulmonary hemorrhage, or gastrointestinal hemorrhage.

The table below shows adverse reactions that occurred in at least 5% of patients receiving INOmax® in the CINRGI study. None of the differences in these adverse reactions were statistically significant when iNO patients were compared to patients receiving placebo.

TABLE 3

ADVERSE REACTIONS ON THE CINRGI TRIAL

| Adverse Reaction | Placebo (n = 89) | Inhaled NO (n = 97) |
|---|---|---|
| Atelectasis | 5 (4.8%) | 7 (6.5%) |
| Bilirubinemia | 6 (5.8%) | 7 (6.5%) |
| Hypokalemia | 5 (4.8%) | 9 (8.3%) |
| Hypotension | 3 (2.9%) | 6 (5.6%) |
| Thrombocytopenia | 20 (19.2%) | 16 (14.8%) |

Post-Marketing Experience. The following AEs have been reported as part of the post-marketing surveillance. These events have not been reported above. Given the nature of spontaneously reported post-marketing surveillance data, it is impossible to determine the actual incidence of the events or definitively establish their causal relationship to the drug. The listing is alphabetical: dose errors associated with the delivery system; headaches associated with environmental exposure of INOmax® in hospital staff; hypotension associated with acute withdrawal of the drug; hypoxemia associated with acute withdrawal of the drug; pulmonary edema in patients with CREST syndrome.

An analysis of AEs and SAEs from both the CINRGI and NINOS studies, in addition to post-marketing surveillance, did not suggest that patients who have pre-existing LVD could experience an increased risk of AEs or SAEs. Nor was it predictable to physicians skilled in the art that patients having pre-existing LVD (possibly identified as those patients having a PCWP greater than 20 mmHg) should be evaluated in view of the benefit versus risk of using iNO in patients with clinically significant LVD, and that these patients should be evaluated on a case by case basis.

Example 1

INOT22 Study

The INOT22 study, entitled "Comparison of supplemental oxygen and nitric oxide for inhalation plus oxygen in the evaluation of the reactivity of the pulmonary vasculature during acute pulmonary vasodilatory testing," was conducted both to assess the safety and effectiveness of INOmax® as a diagnostic agent in patients undergoing assessment of pulmonary hypertension (primary endpoint), and to confirm the hypothesis that iNO is selective for the pulmonary vasculature (secondary endpoint).

During, and upon final analysis of the INOT22 study results, applicants discovered that rapidly decreasing the pulmonary vascular resistance, via the administration of iNO to a patient in need of such treatment, may be detrimental to patients with concomitant, pre-existing LVD. Therefore, a precaution for patients with LVD was proposed to be included in amended prescribing information for INOmax®. Physicians were further informed to consider reducing left ventricular afterload to minimize the occurrence of pulmonary edema in patients with pre-existing LVD.

In particular, the INOT22 protocol studied consecutive children undergoing cardiac catheterization that were prospectively enrolled at 16 centers in the US and Europe. Inclusion criteria: 4 weeks to 18 years of age, pulmonary hypertension diagnosis, i.e. either idiopathic pulmonary hypertension (IPAH) or related to congenital heart disease (CHD) (repaired or unrepaired) or cardiomyopathy, with pulmonary vascular resistance index (PVRI)>3 u·m². Later amendments, as discussed herein, added an additional inclusionary criterion of a PCWP less than 20 gmm Hg. Patients were studied under general anaesthesia, or with conscious sedation, according to the practice of the investigator. Exclusion criteria: focal infiltrates on chest X-ray, history of intrinsic lung disease, and/or currently taking PDE-5 inhibitors, prostacyclin analogues or sodium nitroprusside. The study involved supplemental $O_2$ and NO for inhalation plus $O_2$ in the evaluation of the reactivity of the pulmonary vasculature during acute pulmonary vasodilator testing. Consecutive children undergoing cardiac catheterization were prospectively enrolled at 16 centers in the US and Europe. As hypotension is expected in these neonatal populations, the comparison between iNO and placebo groups is difficult to assess. A specific secondary endpoint was evaluated in study INOT22 to provide a more definitive evaluation.

The primary objective was to compare the response frequency with iNO and $O_2$ vs. $O_2$ alone; in addition, all subjects were studied with iNO alone. Patients were studied during five periods: Baseline 1, Treatment Period 1, Treatment Period 2, Baseline 2 and Treatment Period 3. All patients received all three treatments; treatment sequence was randomized by center in blocks of 4; in Period 1, patients received either NO alone or $O_2$ alone, and the alternate treatment in Period 3. All patients received the iNO and $O_2$ combination treatment in Period 2. Once the sequence was assigned, treatment was unblinded. Each treatment was given for 10 minutes prior to obtaining hemodynamic measurements, and the Baseline Period 2 was at least 10 minutes.

Results for the intent-to-treat (ITT) population, defined as all patients who were randomized to receive drug, indicated that treatment with NO plus $O_2$ and $O_2$ alone significantly increased systemic vascular resistance index (SVRI) (Table 4). The change from baseline for NO plus $O_2$ was 1.4 Woods Units per meter² (WU·m²) (p=0.007) and that for $O_2$ was 1.3 WU·m² (p=0.004). While the change from baseline in SVRI with NO alone was −0.2 WU·m² (p=0.899) which demonstrates a lack of systemic effect.

TABLE 4

SVRI Change From Baseline by Treatment (Intent-to-Treat)

| | Treatment | | |
|---|---|---|---|
| SVRI (WU · m²) | NO Plus $O_2$ (n = 109) | $O_2$ (n = 106) | NO (n = 106) |
| Baseline (room air) | | | |
| Mean | 17.2 | 17.6 | 18.0 |
| Standard Deviation (SD) | 8.86 | 9.22 | 8.44 |
| Median | 15.9 | 16.1 | 16.2 |
| Minimum, maximum | −7.6, 55.6 | −7.6, 55.6 | 1.9, 44.8 |
| Post-treatment | | | |
| Mean | 18.7 | 18.9 | 17.8 |
| SD | 9.04 | 8.78 | 9.40 |

TABLE 4-continued

SVRI Change From Baseline by Treatment (Intent-to-Treat)

| SVRI (WU · m²) | Treatment | | |
|---|---|---|---|
| | NO Plus O₂ (n = 109) | O₂ (n = 106) | NO (n = 106) |
| Median | 17.1 | 17.1 | 15.4 |
| Minimum, maximum | 3.0, 47.4 | 3.9, 43.6 | 3.3, 50.7 |
| Change From Baseline | | | |
| Mean | 1.4 | 1.3 | −0.2 |
| SD | 5.94 | 5.16 | 4.65 |
| Median | 1.2 | 1.0 | 0.2 |
| Minimum, maximum | −20.5, 19.1 | −18.1, 17.7 | −12.5, 12.7 |
| p-value[a] | 0.007 | 0.004 | 0.899 |

Pairwise comparisons
NO plus $O_2$ versus $O_2$, p = 0.952
NO plus $O_2$ versus NO, p = 0.014
$O_2$ versus NO, p = 0.017

[a]p-value from a Wilcoxon Signed Rank Test. Only patients with data to determine response at both treatments are included in this analysis.
Source: INOT22 CSR Table 6.4.1 and Appendix 16.2.6 (ATTACHMENT 1)

The ideal pulmonary vasodilator should reduce PVRI and/or PAPm while having no appreciable effect on systemic blood pressure or SVRI. In this case, the ratio of PVRI to SVRI would decrease, given some measure of the selectivity of the agent for the pulmonary vascular bed. The change in the ratio of PVRI to SVRI by treatment is shown in Table 5.

TABLE 5

Change in Ratio of PVRI to SVRI by Treatment (Intent-to-Treat)

| Ratio PVRI/SVRI | Treatment | | |
|---|---|---|---|
| | NO Plus O₂ (n = 108) | O₂ (n = 105) | NO (n = 106) |
| Baseline | | | |
| Mean | 0.6 | 0.5 | 0.6 |
| SD | 0.60 | 0.45 | 0.56 |
| Median | 0.5 | 0.5 | 0.4 |
| Minimum, Maximum | −1.6, 4.7 | −1.6, 1.8 | 0.0, 4.7 |
| Post Treatment | | | |
| Mean | 0.4 | 0.4 | 0.5 |
| SD | 0.31 | 0.31 | 0.46 |
| Median | 0.3 | 0.4 | 0.3 |
| Minimum, Maximum | 0.0, 1.3 | 0.0, 1.4 | −1.2, 2.2 |
| Change from Baseline | | | |
| Mean | −0.2 | −0.1 | −0.1 |
| SD | 0.52 | 0.31 | 0.54 |
| Median | −0.1 | −0.1 | 0.0 |
| Minimum, Maximum | −4.4, 2.0 | −1.6, 2.0 | −4.4, 1.6 |
| P Value[1] | <0.001 | <0.001 | 0.002 |

[1]Wilcoxon Signed Rank Test
Source: INOT22 CSR Table 6.5.1 (ATTACHMENT 2)

All three treatments have a preferential effect on the pulmonary vascular bed, suggesting that all three are selective pulmonary vasodilators. The greatest reduction in the ratio was during treatment with NO plus $O_2$, possibly due to the decrease in SVRI effects seen with $O_2$ and NO plus $O_2$. These results are displayed as percent change in the ratio (See Table 6).

TABLE 6

Percent Change in Ratio of PVRI to SVRI by Treatment (Intent-to-Treat)

| Ratio PVRI/SVRI | Treatment | | |
|---|---|---|---|
| | NO Plus O₂ (n = 108) | O₂ (n = 105) | NO (n = 106) |
| Baseline | | | |
| Mean | 0.6 | 0.5 | 0.6 |
| SD | 0.60 | 0.45 | 0.56 |
| Median | 0.5 | 0.5 | 0.4 |
| Minimum, Maximum | −1.6, 4.7 | −1.6, 1.8 | 0.0, 4.7 |
| Post Treatment | | | |
| Mean | 0.4 | 0.4 | 0.5 |
| SD | 0.31 | 0.31 | 0.46 |
| Median | 0.3 | 0.4 | 0.3 |
| Minimum, Maximum | 0.0, 1.3 | 0.0, 1.4 | −1.2, 2.2 |
| Percent Change from Baseline | | | |
| Mean | −33.5 | −19.3 | −6.2 |
| SD | 36.11 | 34.59 | 64.04 |
| Median | −34.0 | −21.3 | −13.8 |
| Minimum, Maximum | −122.2, 140.1 | −122.7, 93.3 | −256.1, 294.1 |
| P Value[1] | <0.001 | <0.001 | 0.006 |

[1]Wilcoxon Signed Rank Test
Source: INOT22 CSR Table 6.5.2 (ATTACHMENT 3)

NO plus $O_2$ appeared to provide the greatest reduction in the ratio, suggesting that NO plus $O_2$ was more selective for the pulmonary vasculature than either agent alone.

Overview of Cardiovascular Safety. In the INOT22 diagnostic study, all treatments (NO plus $O_2$, $O_2$, and NO) were well-tolerated. Seven patients of 134 treated experienced an AE during the study. These included cardiac arrest, bradycardia, low cardiac output (CO) syndrome, elevated ST segment (the portion of an electrocardiogram between the end of the QRS complex and the beginning of the T wave) on the electrocardiography (ECG) decreased $O_2$ saturation, hypotension, mouth hemorrhage and pulmonary hypertension (PH). The numbers of patients and events were too small to determine whether risk for AEs differed by treatment, diagnosis, age, gender or race. Eight patients are shown in Table 5 due to the time period in which events are reported. AEs were reported for 12 hours or until hospital discharge (which limits the period in which such events can be reported). There is technically no time limit in which SAEs are to be reported. So, there were 7 AEs during the study and at least one SAE after the study.

A total of 4 patients had AEs assessed as being related to study drug. These events included bradycardia, low CO syndrome, ST segment elevation on the ECG, low $O_2$ saturation, PH and hypotension. All but 2 AEs were mild or moderate in intensity and were resolved. Study treatments had slight and non-clinically significant effects on vital signs including heart rate, systolic arterial pressure and diastolic arterial pressure. When an investigator records an AE, they are required to say if (in their opinion) the event is related to the treatment or not. In this case, 4 of 7 were considered by the investigator to be related to treatment.

The upper limit of normal PCWP in children is 10-12 mm Hg and 15 mm Hg in adults. In INOT22, a baseline PCWP value was not included as exclusion criteria. However, after the surprising and unexpected identification of SAEs in the early tested patients, it was determined that patients with pre-existing LVD had an increased risk of experiencing an AE or SAE upon administration (e.g., worsening of left ventricular function due to the increased flow of blood through the lungs). Accordingly, the protocol for INOT22 was thereafter amended to exclude patients with a baseline PCWP greater than 20 mm Hg after one patient experienced acute circulatory collapse and died during the study. The value "20 mm Hg" was selected to avoid enrollment of a pediatric population with LVD such that they would be most likely at-risk for these SAEs.

SAEs were collected from the start of study treatment until hospital discharge or 12 hours, whichever occurred sooner. Three SAEs were reported during the study period, and a total of 7 SAEs were reported. Three of these were fatal SAEs and 4 were nonfatal (one of which led to study discontinuation). In addition, one non-serious AE also lead to discontinuation. A list of subjects who died, discontinued or experienced an SAE is provided in Table 7 below.

TABLE 7

Subjects that died, discontinued or experienced SAEs

| Patient number | AE | Serious? | Fatal? | Discontinued treatment? |
|---|---|---|---|---|
| 01020 | Desaturation (hypoxia) | No | No | Yes |
| 02002 | Pulmonary edema | Yes | No | No |
| 04001 | Hypotension and cardiac arrest | Yes | Yes | No |
| 04003 | Hypotension and ECG changes | Yes | No | Yes |
| 04008 | Hypotension and hypoxemia | Yes | Yes | No |
| 05002 | Hypoxia and bradycardia (also pulmonary edema) | Yes | Yes | No |
| 07003 | Cardiac arrest | Yes | No | No |
| 17001 | Hypoxia | Yes | No | No |

Two of the 3 fatal SAEs were deemed related to therapy. All 4 non-fatal SAEs were also considered related to therapy. The numbers of patients and events were too small to determine whether risk for SAEs differed by treatment, diagnosis, age, gender or race. At least two patients developed signs of pulmonary edema (subjects 05002 and 02002). This is of interest because pulmonary edema has previously been reported with the use of iNO in patients with LVD, and may be related to decreasing PVRI and overfilling of the left atrium. (Hayward C S et al., 1996, Inhaled Nitric Oxide in Cardiac Failure: Vascular Versus Ventricular Effects, *J Cardiovascular Pharmacology* 27:80-85; Bocchi E A et al., 1994, Inhaled Nitric Oxide Leading to Pulmonary Edema in Stable Severe Heart Failure, *Am J Cardiology* 74:70-72; and, Semigran M J et al., 1994, Hemodynamic Effects of Inhaled Nitric Oxide in Heart Failure, *J Am Coll Cardiology* 24:982-988).

Although the SAE rate is within range for this population, it appears that patients with the most elevated PCWP at baseline had a disproportionately high number of these events. (Bocchi E A et al., 1994; Semigran M J et al., 1994).

In the INOT22 study, 10 of the total 134 patients had a baseline PCWP≥18 mm Hg (7.5%), of which 3 subjects (04001, 02002 and 04003) had a SAE or were prematurely discontinued from the study (30%), compared to 6.5% for the entire cohort.

Although there were very few significant AEs in the INOT22 study, these events are consistent with the expected physiologic changes in patients with severe LVD. The events also corroborate prior observations that iNO is rapidly acting, selective for the pulmonary vasculature, and well-tolerated in most patients. The actual incidence of acute LVD during acute ventricular failure (AVT) is unknown. However, it is reasonable to expect that a significant number of patients are at-risk for an increased incidence of SAES upon iNO treatment based upon the nature of the underlying nature of the illness, i.e., pulmonary hypertension and cardiovascular disease more generally. Thus, it would be advantageous to have physicians identify these patients prior to beginning iNO treatment, so that the physicians are alerted to this possible outcome.

Benefits and Risks Conclusions. The INOT22 study was designed to demonstrate the physiologic effects of iNO in a well defined cohort of children (i.e., intended patient population) with pulmonary hypertension using a high concentration, 80 ppm, of iNO, i.e., one that would be expected to have the maximal pharmacodynamic effect. INOT22 was the largest and most rigorous pharmacodynamic study of iNO conducted to date, and it confirms a number of prior observations, such as iNO's being rapidly acting, selective for the pulmonary vasculature, and well-tolerated in most patients.

It is also acknowledged that rapidly decreasing the PVR may be undesirable and even dangerous in patients with concomitant LVD. In the INOT22 study, the overall numbers of SAES and fatal SAES are within the expected range for patients with this degree of cardiopulmonary disease. The overall rate is 7/124 (5.6%), which is closely comparable to the rate of 6% recently reported in a very similar cohort of patients. (Taylor C J et al., 2007, Risk of cardiac catheterization under anaesthesia in children with pulmonary hypertension, *Br J Anaesth* 98(5):657-61). Thus, the overall rate of SAES would seem to be more closely related to the underlying severity of illness of the patients rather than to the treatments given during this study.

The INOT22 study results demonstrate that patients who had pre-existing LVD may experience an increased rate of SAES (e.g., pulmonary edema). During the course of the study, the protocol was amended to exclude patients with a PCWP>20 mmHg. The benefit/risk of using iNO in patients with clinically significant LVD should be evaluated on a case by case basis. A reduction in left ventricular afterload may perhaps be applied to minimize the occurrence of pulmonary edema.

I claim:

1. A method for treating a pediatric patient who is experiencing idiopathic pulmonary arterial hypertension resulting in oxygen desaturation, wherein the patient is not dependent on right-to-left shunting of blood, the method comprising:
   determining whether the patient has pre-existing left ventricular dysfunction, and
   (a) if the patient does not have pre-existing left ventricular dysfunction, administering to the patient 20 ppm inhaled nitric oxide for a length of time sufficient to improve oxygenation in the patient, and
   (b) if the patient does have pre-existing left ventricular dysfunction, administering inhaled supplemental oxygen to the patient and excluding the patient from treatment with inhaled nitric oxide.

2. A method for treating a pediatric patient who is experiencing oxygen desaturation associated with idiopathic pulmonary arterial hypertension, wherein the patient is not dependent on right-to-left shunting of blood, the method comprising:
   determining whether the patient has pre-existing left ventricular dysfunction, and
   (a) if the patient does not have pre-existing left ventricular dysfunction, administering to the patient 20 ppm inhaled nitric oxide and supplemental oxygen for a length of time sufficient to increase the partial pressure of arterial oxygen (PaO$_2$) in the patient by dilating pulmonary vessels, and (b) if the patient does have pre-existing left ventricular dysfunction, administering inhaled supplemental oxygen to the patient and excluding the patient from treatment with inhaled nitric oxide.

3. A method for treating a pediatric patient who is experiencing oxygen desaturation associated with idiopathic pulmonary arterial hypertension, wherein the patient is not dependent on right-to-left shunting of blood, the method comprising:

evaluating the patient, or having the patient evaluated, to determine if the patient has pre-existing left ventricular dysfunction, and (a) if the patient does not have pre-existing left ventricular dysfunction, administering to the patient 20 ppm inhaled nitric oxide for a length of time sufficient to improve oxygenation in the patient, and (b) if the patient does have pre-existing left ventricular dysfunction, administering inhaled supplemental oxygen to the patient and excluding the patient from treatment with inhaled nitric oxide.

4. A method for treating a pediatric patient who is experiencing oxygen desaturation associated with idiopathic pulmonary arterial hypertension, wherein the patient is not dependent on right-to-left shunting of blood, the method comprising:

administering supplemental oxygen to the patient;

determining whether the patient has pre-existing left ventricular dysfunction; and (a) if the patient does not have pre-existing left ventricular dysfunction, administering to the patient 20 ppm inhaled nitric oxide and supplemental oxygen for a length of time sufficient to increase PaO$_2$ in the patient by dilating pulmonary vessels, and (b) if the patient does have pre-existing left ventricular dysfunction, continuing to administer inhaled supplemental oxygen to the patient, and excluding the patient from treatment with inhaled nitric oxide.

5. The method of claim 1, wherein the risk that inhaled nitric oxide administration will result in pulmonary edema in a pediatric subject is higher if the subject has pre-existing left ventricular dysfunction than if the subject does not have pre-existing left ventricular dysfunction.

6. The method of claim 2, wherein the risk that inhaled nitric oxide administration will result in pulmonary edema in a pediatric subject is higher if the subject has pre-existing left ventricular dysfunction than if the subject does not have pre-existing left ventricular dysfunction.

7. The method of claim 3, wherein the risk that inhaled nitric oxide administration will result in pulmonary edema in a pediatric subject is higher if the subject has pre-existing left ventricular dysfunction than if the subject does not have pre-existing left ventricular dysfunction.

8. The method of claim 4, wherein the risk that inhaled nitric oxide administration will result in pulmonary edema in a pediatric subject is higher if the subject has pre-existing left ventricular dysfunction than if the subject does not have pre-existing left ventricular dysfunction.

9. The method of claim 1, wherein the determining step comprises measuring, or having measured, the patient's pulmonary capillary wedge pressure, and concluding that, if the pulmonary capillary wedge pressure is greater than 20 mmHg, the patient has pre-existing left vermicular dysfunction.

10. The method of claim 2, wherein the determining step comprises measuring, or having measured, the patient's pulmonary capillary wedge pressure, and concluding that, if the pulmonary capillary wedge pressure is greater than 20 mmHg, the patient has pre-existing left ventricular dysfunction.

11. The method of claim 3, wherein the evaluating step comprises measuring, or having measured, the patient's pulmonary capillary wedge pressure, and concluding that, if the pulmonary capillary wedge pressure is greater than 20 mmHg, the patient has pre-existing left ventricular dysfunction.

12. The method of claim 1, wherein the determining step comprises (i) assessing, or having assessed, the patient's clinical signs and symptoms of heart failure; or (ii) using, or having used, echocardiography diagnostic screening.

13. The method of claim 2, wherein the determining step comprises (i) assessing, or having assessed, the patient's clinical signs and symptoms of heart failure; or (ii) using, or having used, echocardiography diagnostic screening.

14. The method of claim 3, wherein the evaluation step comprises (i) assessing, or having assessed, the patient's clinical signs and symptoms of heart failure; or (ii) using, or having used, echocardiography diagnostic screening.

15. The method of claim 1, wherein the pre-existing left ventricular dysfunction of (b) is attributable to congenital heart disease.

16. The method of claim 2, wherein the pre-existing left ventricular dysfunction of (b) is attributable to congenital heart disease.

17. The method of claim 3, wherein the pre-existing left ventricular dysfunction of (b) is attributable to congenital heart disease.

18. The method of claim 1, wherein the pre-existing left ventricular dysfunction of (b) is characterized by systolic dysfunction.

19. The method of claim 2, wherein the pre-existing left ventricular dysfunction of (b) is characterized by systolic dysfunction.

20. The method of claim 3, wherein the pre-existing left ventricular dysfunction of (b) is characterized by systolic dysfunction.

21. The method of claim 4, wherein the pre-existing left ventricular dysfunction of (b) is characterized by systolic dysfunction.

22. The method of claim 1, wherein the pediatric patient is a neonate.

23. The method of claim 2, wherein the pediatric patient is a neonate.

24. The method of claim 3, wherein the pediatric patient is a neonate.

25. The method of claim 1, wherein the pediatric patient is 4 weeks to 18 years of age.

26. The method of claim 2, wherein the pediatric patient is 4 weeks to 18 years of age.

27. The method of claim 3, wherein the pediatric patient is 4 weeks to 18 years of age.

28. The method of claim 22, wherein the neonate has persistent pulmonary hypertension of the newborn (PPHN).

29. The method of claim 23, wherein the neonate has PPHN.

30. The method of claim 24, wherein the neonate has PPHN.

31. The method of claim 1, wherein the improvement in oxygenation of (a) is as indicated by an increase in the patient's PaO$_2$.

32. The method of claim 3, wherein the improvement in oxygenation of (a) is as indicated by an increase in the patient's $PaO_2$.

33. A method for treating a neonate patient with hypoxic respiratory failure associated with clinical or echocardiographic evidence of idiopathic pulmonary arterial hypertension, wherein the patient is not dependent on right-to-left shunting of blood, the method comprising:
determining whether the patient has pre-existing left ventricular dysfunction, and
(a) if the patient does not have pre-existing left ventricular dysfunction, administering to the patient 20 ppm inhaled nitric oxide for a length of time sufficient to improve oxygenation in the patient, and
(b) if the patient does have pre-existing left ventricular dysfunction, administering inhaled supplemental oxygen to the patient and excluding the patient from treatment with inhaled nitric oxide.

34. The method of claim 33, wherein the determining step comprises measuring, or having measured, the patient's pulmonary capillary wedge pressure, and concluding that, if the pulmonary capillary wedge pressure is greater than 20 mmHg, the patient has pre-existing left ventricular dysfunction.

35. The method of claim 33, wherein the pre-existing left ventricular dysfunction of (b) is characterized by systolic dysfunction.

36. The method of claim 33, wherein the improvement in oxygenation of (a) is as indicated by an increase in the patient's $PaO_2$.

37. A method for treating a neonate patient with hypoxic respiratory failure associated with clinical or echocardiographic evidence of idiopathic pulmonary arterial hypertension, wherein the patient is not dependent on right-to-left shunting of blood, the method comprising:
determining whether the patient has pre-existing left ventricular dysfunction, and
(a) if the patient does not have pre-existing left ventricular dysfunction, administering to the patient 20 ppm inhaled nitric oxide and supplemental oxygen for a length of time sufficient to increase $PaO_2$ in the patient by dilating pulmonary vessels, and
(b) if the patient does have pre-existing left ventricular dysfunction, administering inhaled supplemental oxygen to the patient and excluding the patient from treatment with inhaled nitric oxide.

38. The method of claim 37, wherein the determining step comprises measuring, or having measured, the patient's pulmonary capillary wedge pressure, and concluding that, if the pulmonary capillary wedge pressure is greater than 20 mmHg, the patient has pre-existing left ventricular dysfunction.

39. The method of claim 37, wherein the pre-existing left ventricular dysfunction of (b) is characterized by systolic dysfunction.

40. A method for treating a neonate patient with hypoxic respiratory failure associated with clinical or echocardiographic evidence of idiopathic pulmonary arterial hypertension, wherein the patient is not dependent on right-to-left shunting of blood, the method comprising:
determining whether the patient has pre-existing left ventricular dysfunction, and
(a) if the patient does not have pre-existing left ventricular dysfunction, administering to the patient 20 ppm inhaled nitric oxide for a length of time sufficient to improve oxygenation in the patient, and
(b) if the patient does have pre-existing left ventricular dysfunction, treating the patient with inhaled supplemental oxygen or extracorporeal membrane oxygenation, and excluding the patient from treatment with inhaled nitric oxide.

41. The method of claim 40, wherein the determining step comprises measuring, or having measured, the patient's pulmonary capillary wedge pressure, and concluding that, if the pulmonary ca.pillary wedge pressure is greater than 20 mmHg, the patient has pre-existing left ventricular dysfunction.

42. The method of claim 40, wherein the pre-existing left ventricular dysfunction of (b) is characterized by systolic dysfunction.

43. The method of claim 40, wherein the improvement in oxygenation of (a) is as indicated by an increase in the patient's $PaO_2$.

* * * * *

UNITED STATES PATENT AND TRADEMARK OFFICE
CERTIFICATE OF CORRECTION

| | | |
|---|---|---|
| PATENT NO. | : 11,931,377 B2 | Page 1 of 1 |
| APPLICATION NO. | : 16/378361 | |
| DATED | : March 19, 2024 | |
| INVENTOR(S) | : James S. Baldassarre | |

It is certified that error appears in the above-identified patent and that said Letters Patent is hereby corrected as shown below:

In the Claims

Column 15, Line 66: In Claim 9, delete "vermicular" and insert -- ventricular --.

Column 18, Line 33: In Claim 41, delete "ca.pillary" and insert -- capillary --.

Signed and Sealed this
Fourteenth Day of May, 2024

Katherine Kelly Vidal
*Director of the United States Patent and Trademark Office*